United States Patent
Goldfine et al.

(10) Patent No.: US 6,188,218 B1
(45) Date of Patent: Feb. 13, 2001

(54) ABSOLUTE PROPERTY MEASUREMENT WITH AIR CALIBRATION

(75) Inventors: Neil J. Goldfine, Newton; Darrell E. Schlicker, Watertown, both of MA (US); Andrew P. Washabaugh, Menlo Park, CA (US)

(73) Assignee: Jentek Sensors, Inc., Watertown, MA (US)

( * ) Notice: Under 35 U.S.C. 154(b), the term of this patent shall be extended for 0 days.

(21) Appl. No.: 09/182,693

(22) Filed: Oct. 29, 1998

Related U.S. Application Data

(60) Provisional application No. 60/063,534, filed on Oct. 29, 1997, provisional application No. 60/069,604, filed on Dec. 15, 1997, and provisional application No. 60/104,526, filed on Oct. 16, 1998.

(51) Int. Cl.[7] .......................... G01N 27/72; G01N 27/82; G01R 33/12
(52) U.S. Cl. .......................... 324/243; 324/202; 324/242; 324/230; 324/262
(58) Field of Search .......................... 324/202, 207.17, 324/207.18, 207.19, 207.26, 225, 227, 229–233, 239–243, 262; 340/870.32

(56) References Cited

U.S. PATENT DOCUMENTS

| | | | |
|---|---|---|---|
| 3,249,854 | 5/1966 | Nevius | 340/870.32 |
| 3,721,859 | 3/1973 | Blanyer | 361/236 |
| 3,939,404 | 2/1976 | Tait | 324/224 |
| 4,058,766 | 11/1977 | Vogel et al. | 324/667 |
| 4,355,300 | 10/1982 | Weber | 235/451 |
| 4,399,100 | 8/1983 | Zsolnay et al. | 422/62 |
| 4,423,371 | 12/1983 | Senturia et al. | 324/662 |
| 4,496,697 | 1/1985 | Zsolnay et al. | 526/60 |
| 4,757,259 | 7/1988 | Charpentier | 324/227 |
| 4,799,010 | 1/1989 | Muller | 324/240 |
| 4,810,966 | 3/1989 | Schmall | 324/207.17 |
| 4,814,690 | 3/1989 | Melcher et al. | 324/674 |
| 4,853,617 | 8/1989 | Douglas et al. | 324/67 |

(List continued on next page.)

FOREIGN PATENT DOCUMENTS

| | | |
|---|---|---|
| 0 242 947 | 10/1987 | (EP) . |
| 0 723 166 A1 | 7/1996 | (EP) . |
| 2 031 155A | 4/1980 | (GB) . |
| 502205 | of 1976 | (SU) . |
| 578609 | of 1977 | (SU) . |
| 894547 | of 1981 | (SU) . |
| 1095101 | of 1984 | (SU) . |
| WO 92/03090 | 3/1992 | (WO) . |

OTHER PUBLICATIONS

Goldfine, Neil et al., "Dielectrometers and magnetometers, suitable for in–situ inspection of ceramic and metallic coated components," SPIE Conference, Jun. 1995, 11 pages.

(List continued on next page.)

*Primary Examiner*—Jay Patidar
(74) *Attorney, Agent, or Firm*—Hamilton, Brooks, Smith & Reynolds, P.C.

(57) ABSTRACT

An instrument and method for providing accurate and reproducible measurement of absolute properties of a material under test without using conductivity or crack calibration standards. The instrument has a sensor designed to minimize unmodeled parasitic effects. To accomplish this, the sensor has one or more of the following features: dummy secondary elements located at the ends of a primary winding meandering, setting back of the sensing element from a connecting portion of the primary winding, or various grouping of secondary elements. The sensing elements of the sensor can be connected individually or in differential mode to gather absolute or differential sensitivity measurements. In addition, the instrumentation is configured such that a significant portion of the instrumentation electronics is placed as close to the sensor head to provide independently controllable amplification of the measurement signals therein reducing noise and other non-modeled effects.

44 Claims, 24 Drawing Sheets

U.S. PATENT DOCUMENTS

| | | |
|---|---|---|
| 4,883,264 | 11/1989 | Yoshikawa et al. ............... 271/110 |
| 4,912,414 | 3/1990 | Lesky et al. ......................... 324/329 |
| 4,922,201 | 5/1990 | Vernon et al. ....................... 324/236 |
| 5,015,951 | 5/1991 | Melcher ............................... 324/232 |
| 5,041,785 | 8/1991 | Bogaerts et al. ................ 324/207.24 |
| 5,059,902 | 10/1991 | Linder ............................. 324/207.17 |
| 5,086,274 | 2/1992 | Gobin et al. ......................... 324/239 |
| 5,182,513 | 1/1993 | Young et al. ........................ 324/232 |
| 5,204,621 | 4/1993 | Hermann et al. ............... 324/207.18 |
| 5,237,271 | 8/1993 | Hedengren ........................... 324/232 |
| 5,262,722 | 11/1993 | Hedengren et al. ................. 324/242 |
| 5,278,498 | 1/1994 | Vernon et al. ....................... 324/234 |
| 5,293,119 | 3/1994 | Podney ................................. 324/242 |
| 5,315,234 | 5/1994 | Sutton, Jr. et al. .................. 324/242 |
| 5,345,514 | 9/1994 | Mahdavieh et al. ................ 382/152 |
| 5,363,051 | 11/1994 | Jenstrom et al. .................... 324/661 |
| 5,371,461 | 12/1994 | Hedengren ........................... 324/225 |
| 5,371,462 | 12/1994 | Hedengren et al. ................. 324/225 |
| 5,373,245 | 12/1994 | Vranish ................................ 324/662 |
| 5,389,876 | 2/1995 | Hedengren et al. ................. 324/242 |
| 5,418,457 | 5/1995 | Hedengren et al. ................. 324/225 |
| 5,434,504 | 7/1995 | Hollis et al. .................... 324/207.17 |
| 5,442,347 | 8/1995 | Vranish .......................... 340/870.37 |
| 5,453,689 | 9/1995 | Goldfine et al. .................... 324/239 |
| 5,463,201 | 10/1995 | Hedengren et al. ............ 219/121.83 |
| 5,485,084 | 1/1996 | Duncan et al. ...................... 324/225 |
| 5,541,510 | 7/1996 | Danielson ............................ 324/233 |
| 5,629,621 | 5/1997 | Goldfine et al. .................... 324/239 |

OTHER PUBLICATIONS

Goldfine, Neil et al., "A New Eddy–Current Based Technology for Repeatable Residual Stress and Age Degradation Monitoring," ASNT International Chemical and Petroleum Industry Inspection Technology IV, Houston, TX Jun. 19–22, 1995, 5 pages.

Krampfner, Yehuda D. and Johnson, Duane D., "Flexible Substrate Eddy Current Coil Arrays," Review of Progress in Quantitative Nondestructive Evaluation, vol. 7A, 1988. pp. 471–478.

Zaretsky, M., et al., "Modal Approach to Obtaining Continuum Properties From Inter–Digital Electrode Dielectrometry," Massachusetts Institute of Technology, Lees Technical Report, Jul. 1986, pp. 1–43.

Dodd, V.C. and Deeds, W.E., "Absolute Eddy–Current Measurement of Electrical Conductivity," From "Review of Progress in Quantitative Nondestructive Evaluation," vol. 1, 1982, pp. 387–394.

Dodd, C.V. and Simpson, W.A., "Measurement of Small Magnetic Permeability Changes by Eddy Current Techniques," presented at the National Fall Conference of the American Society for Nondestructive Testing, Oct. 19–22, 1970, pp. 217–221.

Rose, James H. and Nair, Satish M., "Exact recovery of the DC electrical conductivity of a layered solid," Inverse Problems, Letter to the Editor, 1991, pp. L31–L36.

Auld, B.A. et al., "Eddy–Current Signal Analysis and Inversion for Semielliptical Surface Cracks,"Journal of Nondestructive Evaluation, vol. 7, No. 1/2, 1988, pp. 79–94.

Goldfine, Neil and Roach, Dennis, "Early Stage and Widespread Fatigue Damage Assessment for Aircraft Structures and Engines, Using a New Conformable Multiple–Frequency Eddy Current Sensor," ATA NDT Forum, Indianapolis, IN Sep. 8–11, 1997, pp. 1–13.

Goldfine, Dr. Neil J., "Early Stage Fatigue Detection with Application to Widespread Fatigue Damage Assessment in Military and Commercial Aircraft,"DOD/FAA/NASA Conference on Aging Aircraft, Ogden, UT, Jul. 8–10, 1997, pp. 1–10.

Goldfine, Neil J., "Magnetometers for Improved Materials Characterization in Aerospace Applications," Materials Evaluation, Mar. 1993, pp. 396–405.

Goldfine, Neil and Clark, David, "Near Surface Material Property Profiling for Determination of SCC Susceptibility," EPRI Balance–of–Plant Heat Exchanger NDE Symposium, Jackson Hole, WY, Jun. 10–12, 1996.

Morrison, Philip and Tsipis, Kosta, "New Hope in the Minefields," Massachusetts Institute of Technology's *Technology Review*, ISSN 0040–1692, vol. 100, No. 7, pp. 38–47.

"Innovations in Quantitative Nondestructive Evaluation," JENTEK Sensors, Inc. Brochure, No Date Available.

Goldfine, Neil et al., "Surface–Mounted Eddy–Current Sensors For On–Line Monitoring of Fatigue Tests and For Aircraft Health Monitoring," Second Joint NASA/FAA/DoD Conference on Aging Aircraft, Aug. 1998, pp. 1–16.

Goldfine, Neil, "Uncalibrated, Absolute Property Estimation and Measurement Optimization for Conducting and Magnetic Media Using Imposed $\omega$–k Magnetometry," Doctoral Thesis, Cataloged into the Massachusetts Institute of Technology Libraries on Oct. 6, 1992, pp. 1–139.

Miyakawa, Tasuo and Honjo, Ken, "Development of Instrument Detecting Nonmetal Foreign Bodies in Food Material," IEEE Transactions on Instrumentation and Measurement, Apr. 1994, pp. 359–362.

ABSOLUTE PROPERTY MEASUREMENT WITH AIR CALIBRATION

RELATED APPLICATIONS

This application claims the benefit of provisional application 60/063,534, filed Oct. 29, 1997, provisional application 60/069,604 filed Dec. 15, 1997, and provisional application 60/104,526 filed Oct. 16, 1998, the entire teachings of are incorporated herein by reference.

BACKGROUND OF THE INVENTION

The technical field of this invention is magnetometry and, in particular, the nondestructive electromagnetic interrogation of materials of interest to deduce their physical properties and to measure kinematic properties such as proximity. The disclosed invention applies to both conducting and magnetic media.

Conventional application of magnetometers, specifically eddy current sensors, involves the excitation of a conducting winding, the primary, with an electric current source of prescribed temporal frequency. This produces a time-varying magnetic field at the same frequency. The primary winding is located in close proximity to the material under test (MUT), but not in direct contact with the MUT. This type of nondestructive electromagnetic interrogation is sometimes called near field measurement. The excitation fields and the relevant spatial and temporal variations of those fields are quasistatic. The magnitude and phase (or the real and imaginary parts) of the impedance measured at the terminals of the primary winding (i.e., the measured voltage at the primary winding terminals divided by the imposed current) or the transimpedance (i.e., the voltage measured at a secondary winding terminal divided by the imposed current in the primary winding) is used to estimate the MUT properties of interest.

The time-varying magnetic field produced by the primary winding induces currents in the MUT that produce their own magnetic fields. These induced fields have a magnetic flux in the opposite direction to the fields produced by the primary. The net result is that conducting MUTs tend to exclude the magnetic flux produced by the primary windings. The measured impedance and transimpedance at the terminals of the sensor windings are affected by the following: the proximity to the MUT, the physical properties (e.g., permeability and conductivity) of the MUT and the spatial distribution of those properties; the geometric construct of the MUT; other kinematic properties (e.g., velocity) of the MUT; and the existence of defects (e.g., cracks, corrosion, impurities).

The distribution of the currents induced within conducting MUTs and the associated distribution of the magnetic fields in the MUT, in the vicinity of the MUT, and within the conducting primary and secondary windings are governed by the basic laws of physics. Specifically, Ampere's and Faraday's laws combined with Ohm's law and the relevant boundary and continuity conditions result in a mathematical representation of magnetic diffusion in conducting media and the Laplacian decay of magnetic fields. Magnetic diffusion is a phenomena that relates the distribution of induced currents in conducting materials to the distribution of the imposed and induced magnetic fields. Laplacian decay describes the manner in which a magnetic field decays along a path directed away from the original field source.

Magnetometers, such as eddy current sensors, exploit the sensitivity of the impedance or transimpedance (measured at the sensor winding terminals) to the physical and geometric properties of the MUT. This is sometimes accomplished by using multiple temporal excitation frequencies. As the primary winding excitation frequency is increased, the currents in a conducting MUT exclude more and more flux until all the induced currents in the MUT are confined to a thin layer near the surface of the MUT. At frequencies for which the induced currents are all at the surface of the MUT, the MUT can be represented theoretically as a perfect conductor. In other words, at high enough frequency, variations in the conductivity of the MUT will no longer affect the impedance or transimpedance measured at the sensor windings.

This effect has been used in proximity measurement relative to a conducting media. Measurement of proximity to a metal surface is possible at a single excitation frequency, if that frequency is high enough that the MUT can be treated as a perfect conductor. For proximity measurement at lower frequencies, it is necessary to account for the effects of the conductivity of the MUT on the measured impedance, either by physical modeling or by calibration.

In applications requiring the measurement of conductivity, it is necessary to operate at frequencies low enough that the measurements at the terminals of the conducting windings are sensitive to the MUT conductivity. Such applications include the monitoring of aging in conducting media, as well as the direct measurement of conductivity for quality monitoring in metal processing and manufacturing process control. For example, the accurate measurement of the case depth (e.g., the thickness of a heat-affected zone at the surface of a metal after heat treatment) requires a sensor winding geometry and excitation conditions (e.g., frequency, proximity to the MUT) that produce the required sensitivity to the conductivity and thickness of the heat-affected zone.

Two methods are available for determining the desired conditions: (1) experimentation and calibration, and (2) physical modeling and response prediction from basic principals. In practice, each of these techniques has met with some success. The principal limitations of experimentation and calibration are the need for fabrication of expensive calibration test pieces (standards) for each new application, the relatively small dynamic range (i.e., the small range of permissible MUT property variations over which the measurement specifications can be met), and the inaccuracies produced by variation in uncontrolled conditions such as temperature and lift-off errors.

The principal limitations of the physical modeling approach are the inaccuracies introduced by modeling approximations and the existence of unmodeled effects. These limitations are most severe for sensor winding constructs that are not specifically designed to minimize unmodeled effects.

In spite of these limitations, the successful use of conducting windings driven by a current source, as in eddy current sensors, to measure physical and kinematic properties has been widely demonstrated.

For example, eddy current sensors have been used to measure the thickness of conducting strips of known conductivity, as disclosed in Soviet Patents 578,609 and 502,205. Eddy current sensors have also been used for flaw detection, as disclosed in U.S. Pat. No. 3,939,404. Other eddy current sensor applications include measurement of the conductivity-thickness product for thin conducting layers, measurement of the conductivity of conducting plates using calibration standards, and measurement of proximity to conducting layers. Such sensors are also used in proximity measurement for control of machines and devices.

The ability to resolve distributions of parameters and properties of different layers in multi-layered materials has been addressed in U.S. Pat. No. 5,015,95 1. The, referenced patent introduced the concept of multiple wave-number magnetic interrogations of the material of interest, by imposing several different spatial magnetic field excitations, using multiple preselected sensor winding constructs, each with a different wavelength.

SUMMARY OF THE INVENTION

It is recognized that there is a need for measurement methods that provide estimates of the actual physical properties of the MUT. Current techniques often measure "effective" properties that are only indirectly related to the actual physical properties (e.g., permeability and conductivity at a specified excitation frequency). These "effective" property measurements often provide insufficient characterization of the MUT. For example, multiple temporal excitation frequencies are often used to obtain estimates of conductivity or permeability. This is not acceptable if these physical properties vary with temporal excitation frequency. In applications such as monitoring of aging and fatigue in ferrous and nonferrous metal alloys, it may be necessary to completely characterize the dispersive properties of the MUT, including the variations of conductivity and permeability with temporal excitation frequency. U.S. Pat. Nos. 5,015, 951; 5,453,689; and 5,629,621 describe methods for such dispersive property measurement. However, the robustness of these earlier improvements is limited by the presence of unmodeled sensor and material behavior. There is a need for methods and sensors that can provide accurate and reproducible measurement of absolute properties without using conductivity or crack calibration standards. This will reduce errors caused by variations in sensor placement (e.g., lift-off) during calibration, variations in calibration standard properties that are uncontrolled, and human error.

Another enhancement that would extend the measurement performance capability of magnetometers is the ability to calibrate in air. This calibration accounts for instrument drift and unmodeled sensor behavior, which includes cable capacitance variations and manufacture or service created probe-to-probe variations. Often, variability in the manufacture of a given probe design is significant enough to require calibration on standards that have material properties and shape similar to the material under test. The ability to calibrate in air eliminates the inherent limitations of these standards. Other advantages include a reduced opportunity for human error in the selection of the property standards, self-consistently accounting for temperature variation since the calibration is not dependent upon any temperature variations in the standards, and self-consistently removing frequency-to-frequency variations without corrupting the calibration through the use of non-uniform reference standards. These advantages of an air calibration capability can lead to improved robustness and reproducibility of the measurements, reduced costs with the elimination of logistics issues for standards, and the capability for robust, self-consistent component-to-component comparisons with trend analysis.

It is desired to have magnetometers that can robustly provide absolute measurements of the material properties with minimal calibrations. In particular it is desired to have a sensor that does not require an extensive set of training or reference parts for calibration, that may also be required to have the same shape as the component to be tested. This can be accomplished with a sensor that is designed to minimize unmodeled parasitic effect so that only the response of the sensor to an insulating nonmagnetic material such as air can provide the necessary calibration information. While previous sensor designs did support "air calibration," this invention introduces several new improvements. Design modifications to the sensor that minimize the unmodeled effects include altering the layout for the primary and secondary windings, utilizing an equivalent circuit model to account for the parasitic effects on the sensor response, and constructing electrical instrumentation that can extend the dynamic range of the sensor.

In one embodiment, dummy secondary elements are located at the ends of the primary winding meanders to help maintain the periodicity of the magnetic field as viewed by the end sensing elements. This adds to the inclusion of an extra "meandering" at the ends of the primary as described in U.S. patent application Ser. No. 08/702,276 entitled, "Meandering Winding Test Circuit," filed Aug. 23, 1996 by Goldfine et al. which issued on Aug.11, 1998 as U.S. Pat. No. 5,793,206, the entire contents of which are incorporated herein by reference. These "dummy secondary" elements consist of single etched leads that are slightly longer than the lengths of the actual secondary elements, and are introduced to match the periodicity of the mode. Alternative embodiments include making the dummy elements identical in shape and layout to the actual secondary elements, except the leads to the dummy elements are not added so that the dummy loops are not closed. These dummy elements match the periodicity of the actual secondary elements.

Another improvement is the setting back of the sensing element from the connecting portions of the primary winding by one-quarter to one-half of a wavelength. This setting back assures that less than 10% (depending on the number of meandering and height of the sensing element) of the total magnetic flux linked by the sensing element is attributed to the current flowing through the connecting element. The increasing of the setback distance reduces the linked flux from the connecting elements.

Minimizing the distance between secondary winding leads outside of the main footprint area of the windings is another improvement. This reduces stray coupling of unmodeled magnetic flux to the secondary elements. The shouldering of the sensing elements and keeping a close distance between the leads over the remaining distances to the edge of the sensor is a preferred embodiment.

Grouping of secondary elements provides an imaging capability across the footprint of the sensor. In one embodiment, the pixels are overlapping in a manner suitable for continuous monitoring of the movement of an edge of material across the sensor. This can also be accomplished in an embodiment with non-overlapping pixel elements. In this embodiment, a pixel includes combining together secondary sensing elements from both sides of the primary winding. Such sensors are well suited for both surface scanning "contact and non-contact" and permanent surface mounted or imbedded sensor applications.

Another improvement is the use of additional sensing elements which allow for detecting the edge of the material under test. One embodiment that accomplishes this function has a smaller number of secondary elements near the edges of an array connecting together. Another embodiment provides an output from each individual secondary element so that the pixel size is minimized.

Increasing the gap between sensing elements and drive elements reduces coupling of shorter wavelength modes and increases the depth of sensitivity for the sensor. One of the objectives of the meandering winding sensor construction was to create a spatially periodic magnetic field that could couple into the material under test. With any sensor that has discrete dimensions for the windings, higher order spatial modes than the fundamental mode will also be created. The effects of these higher order modes on the response of the sensor can be reduced by increasing the gap between the sensing elements and the drive elements.

Utilizing an equivalent circuit model for the response of the sensor allows for the determination of a scale factor and parasitic impedance, as necessary, that compensate for probe-to-probe variability, drift in the electronic instrumentation, and varying connector cable lengths. This is accomplished through the use of measurements of the sensor response in air, measurements of the response of shunt probes that have the leads to the secondary elements severed and shorted together, and, in some instances, reference parts.

Reconfiguring the placement of the electronics and the probe structure leads to more robust and repeatable property measurements. Moving a significant portion of the instrumentation electronics as close as possible to the sensor head provides independently controllable amplification of the measurement signals which reduces the effects of the connector cables. This may involve splitting the electronics between the probe housing and a remote instrument model (RNM) or satellite box placed between the probe and the data acquisition system In addition, using fixturing and molded structures to rigidly hold the shielding and wiring in place prevents movement of the shielding and wiring after calibration, thus reducing the unmodeled changes in the sensor behavior.

In scan mode, the improved sensor provides the same response (conductivity change) in response to a discrete anomaly at any place in the footprint. The sharpness of the "sensor edge" determines the spatial resolution of a scanned image. Moving an array back and forth by only the width of the footprint of the smallest group of sensing elements, permits substantial improvement of the conductivity (or crack) image resolution. Designing the sensor windings to provide the "sharpest edge" is the key. The width of this edge is the limiting factor in determining image resolution.

Sensing elements can be connected either individually or in differential mode where their signals are subtracted. Including one absolute (individual) connection in an array format with several differential elements permit the robustness (e.g., lift-off compensation) of absolute sensing and the improved sensitivity (amplification) possible with differential measurements. This eliminates the need to control lift-off at each element. Lift-off can vary from element to element and is simply measured at each element using measurement grids.

The ability to absolutely measure lift-off over a wide lift-off range supports the determination of an object's shape. For example, when scanning a cylinder, the sensor might be fixed at a given radius and scanned around the circumference. The variations in lift-off measured by the sensor might then be used to determine the actual shape of a cylindrical part.

If absolute properties can be measured with calibration in air only, then correlation standards can be used to relate the absolute properties (e.g., conductivity) to other properties such as shotpeen intensity, residual stress, temperature, hardness, or crack depth. The correlation standards can be simple flat standards, if the absolute measurements are performed accurately over a wide lift-off range using a conformable eddy current sensor.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

It is a desire to measure properties of a material such as (1) porosity of thermal spray coatings, (2) fatigue in stainless steel, (3) plastic deformation in aluminum and titanium, (4) temperature, (5) surface roughness, (6) plastic deformation, (7) fatigue damage, and (8) corrosion. It has been shown that electrical conductivity of the material varies with these properties. See paper entitled, "Surface-Mounted Eddy-Current Sensors for On-Line Monitoring of Fatigue Tests and for Aircraft Health Monitoring" by Goldfine, Schlicker, and Washabaugh, presented at the Second Joint NASA/FAA/DoD Conference on Aging Aircraft in August 1998 and a paper entitled, "Conformable Eddy Current Sensors and Methods for Gas Turbine Inspection and Health Monitoring" by Goldfine, Washabaugh, Walrath, Zombo, and Miller, presented at the ASM Gas Turbines Technology Conference in October 1998, the entire contents of which are incorporated here by reference. By producing and introducing into the material under test an electromagnetic quasistatic field and detecting (sensing) the resulting field, properties of the material, including those listed above, can be determined by conducting analysis as described below.

It is recognized that the better the sensor and material are modeled, the more accurate and quickly the results can be obtained. Therefore, it is desired to improve the measurement equipment.

Figure 1:
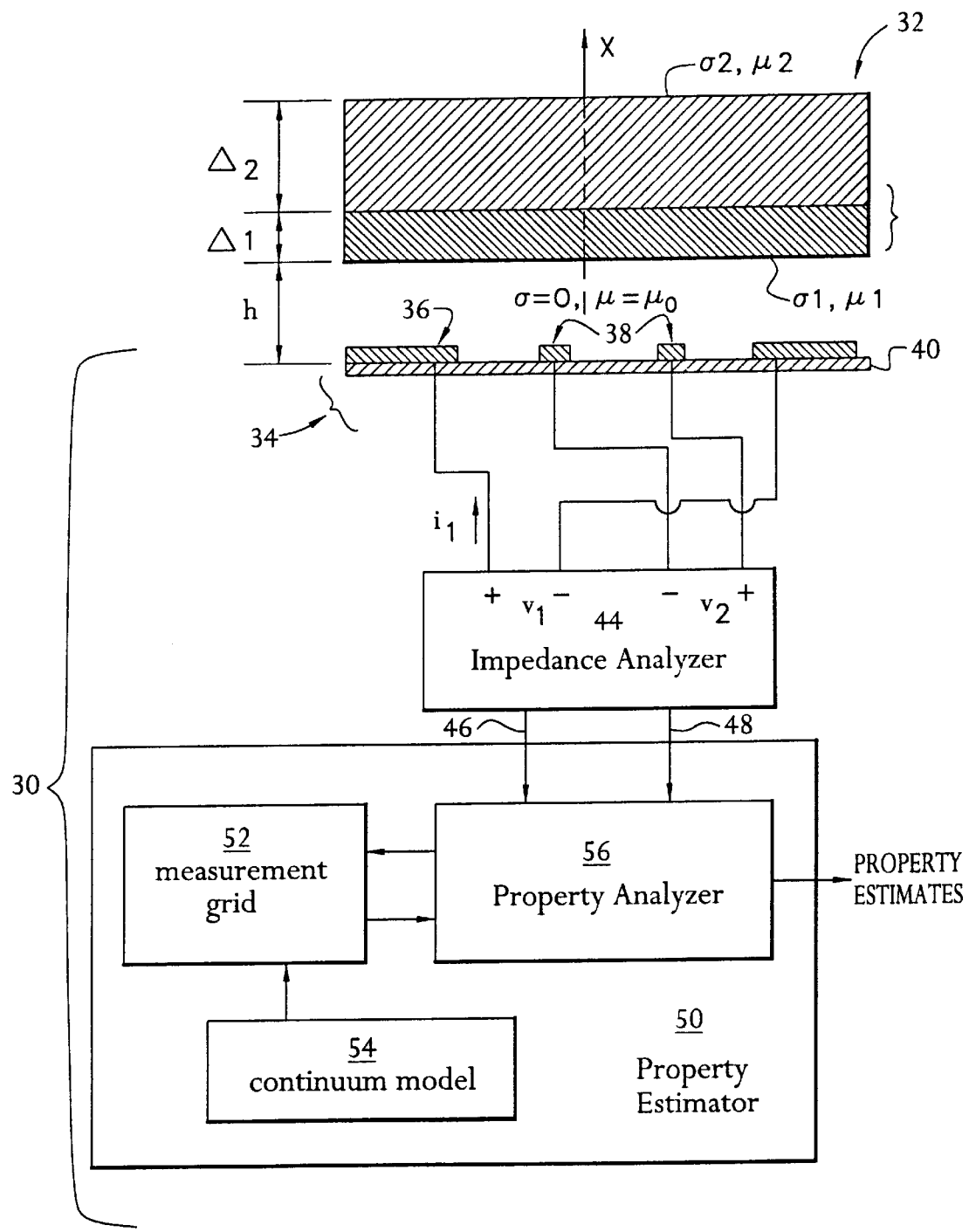
FIG. 1 is a schematic of an instrument and a material under test. Various components of the instrument are shown schematically.

FIG. 1 shows a schematic of an instrument or apparatus 30 for conducting non-destructive testing of a material under test MUT 32. The instrument 30 includes a sensor or an electromagnetic element 34 comprised of a primary winding 36, a sensing or secondary element 38, and an insulating substrate 40. In a preferred embodiment, the sensor has a foam backing to provide conformability to curved or flat parts, and is formed into a sensor tip, such as in FIG. 21, that can be replaced easily if damaged.

The primary winding 36 (also called the driven winding) is driven by an input current or voltage source at a temporal excitation frequency, f, measured in cycles per second where f=ω/2π and ω is the angular frequency of the input electric signal, measured in radians per second.

The sensing or secondary element 38 comprises of a plurality of elements interposed between legs of the primary winding 36. The plurality of elements of the sensing element 40 can be connected in series or in various groups as explained below, in reference to FIGS. 3–8. The voltage induced at the terminals of the series or the respective groups of the sensing element 40 divided by the current applied to the primary winding 36 is called the transimpedance (or transfer impedance). The sensing element can be connected in absolute or differential modes.

The transimpedance is measured by an impedance analyzer 44. The impedance analyzer 44 inputs the current into the primary winding 36. The magnitude 46 and phase 48 of the transimpedance are inputs to a property analyzer 56 of a property estimator 50 which uses a measurement grid 52 to estimate pre-selected properties of a single or multiple layered MUT 32. The measurement grid 52 can be generated either with a continuum model 54 or through experimental measurements on calibration test pieces. The model measurement grid(s), and the property analyzer 56 are part of a property estimator 50 that converts measurements at the sensor terminals for single or multiple operating points (e.g., multiple temporal excitation frequencies) to estimates of pre-selected MUT properties of interest.

The use of an electromagnetic element 34, the impedance analyzer 44, and the property estimator 50 including property analyzer 56, measurement grid(s) 52 and continuum model 54 is described in U.S. patent application Ser. No. 07/803,504, entitled, "Magnetometer Having Periodic Winding Structure and Material Property Estimator" filed on Dec. 6, 1991 by Goldfine and Melcher which issued on Sep. 26, 1995 as U.S. Pat. No. 5,453,689, the entire contents of which are incorporated herein by reference.

In a preferred embodiment, the impedance analyzer 44 is a Hewlett Packard HP4285, JENTEK Sensor Instrument Board, or similar. The property estimator 50 is a computer using a program to perform the analysis and control the impedance analyzer 44.

Figure 2:
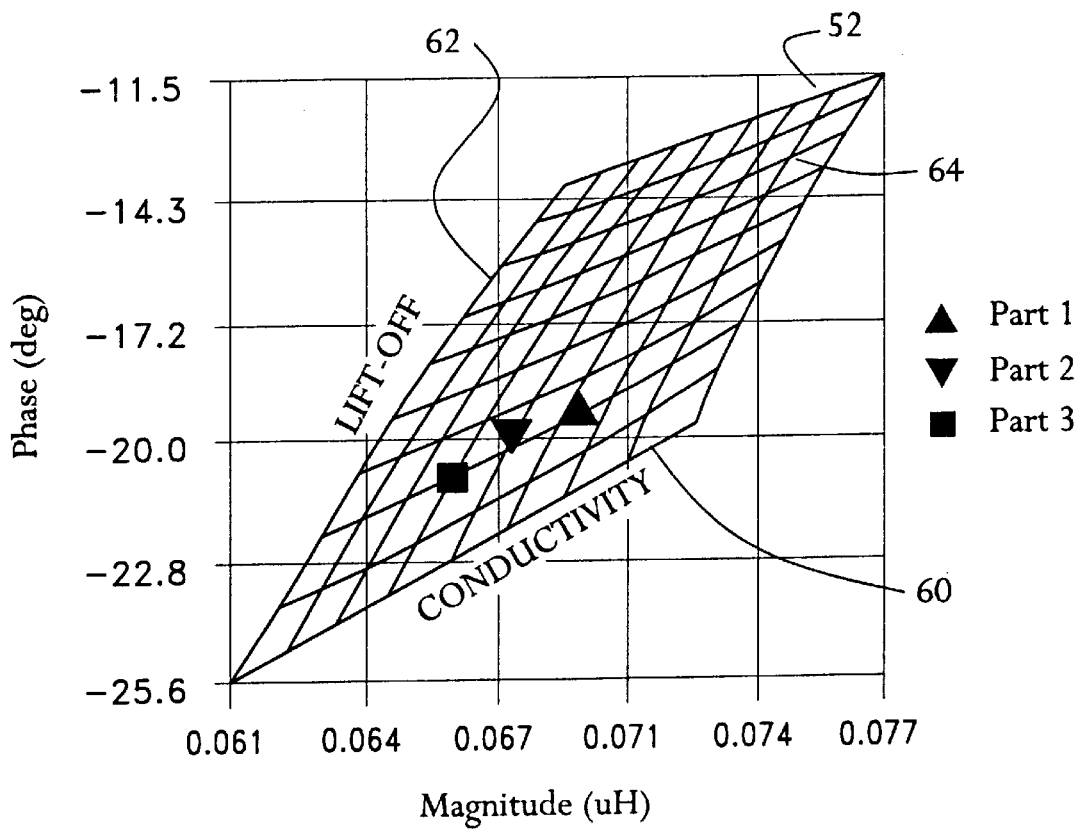
FIG. 2 shows a measurement grid resulting from use of the instrumentation.

FIG. 2 shows a two-dimensional measurement grid, such as described as reference numeral 52 in FIG. 1, with unknown properties (1) electrical conductivity 60 and (2) lift-off 62. A grid point 64 is located at the intersection of each pair of grid lines. Three sets of "measurement data points" taken from sensor impedance magnitude and phase are also represented by the sets of squares and two sets of triangles. This chart shows actual data in which each set contains five measurements that are coincident in the figure because of high measurement repeatability.

Grid tables can be of one, two, three or more dimensions. For example, grid tables of one dimension can include estimates of electrical conductivity varying by frequency, or a dependent property such as porosity varying by frequency. Two-dimensional grids can include, but are not limited to, estimates of (1) electrical conductivity and lift-off (defined to be the distance between the sensor and the material under test); (2) electrical conductivity and layer (or coating) thickness; (3) layer thickness and lift-off; (4) magnetic susceptibility and electrical conductivity; or (5) the real part of the magnetic susceptibility and the imaginary part of the magnetic susceptibility. Two examples of three-dimensional grids are (1) electrical conductivity, lift-off, and layer thickness and (2) electrical conductivity, magnetic susceptibility, and lift-off. These three-dimensional grids require that multiple measurements be made at different lift-offs or with multiple sensor geometry configurations or that a series of two-dimensional grids such as those listed above, be calculated for different operating frequencies, sensor geometries, or lift-offs.

However, prior to taking measurements the instrument 30, including sensor 34, must be calibrated. The calibration is required because of the variation in sensors, instrument (e.g., instrument drift), and cable (e.g., cable capacitance). In addition, the environmental conditions existing at the time of measurement may affect some of the electrical properties being measured. Environmental conditions, such as the temperature of the material being measured or a reference part used for calibration, may be monitored and recorded while making measurements.

Measurement grids, such as shown in FIG. 2, can be calibrated using measurements in air or on reference parts. In a reference part calibration, the objective is to vary at least one of the "unknown" properties during calibration to ensure that the measurement grid is correctly aligned. For example, in a conductivity/lift-off grid, the lift-off can be varied during calibration, using shims of known or unknown thickness. This will establish the correct orientation for the grid.

In a preferred embodiment, the instrument 30 including the sensor 34 are calibrated by an air-calibration method. The sensor 34 is moved away from the material under test and other objects. A current is introduced into the primary winding 36. The corresponding magnetic field induces a magnetic field in the material under test that results in a voltage on the sensing element 38 that is measured using the impedance analyzer 44. The phase and magnitude can then be compared to the measurement grid to determine offset and scale factors that anchor the data onto the grid. The phase and magnitude is compared to the measurement grid. For air calibration, only the infinite lift-off point is needed to estimate the variations in the cable, sensors, and instrument parameters. This eliminates errors caused by operators and poor calibration standards.

Also, offsets, scale factors, or parasitic impedance due to instrument drift or uncalibrated behavior can be computed and used later to shift the measurement data. In addition, the conductivity might be varied during calibration or as part of a measurement procedure to establish the orientation of a line of constant lift-off. By varying the part temperature the conductivity will vary with the lift-off remaining constant. For other grid types, such as a conductivity permeability grid, the permeability might be varied during calibration by applying a bias magnetic field. This would permit alignment of the lines of constant conductivity (along which only the permeability will vary). During measurement procedures it is also desirable to make multiple measurements at multiple operating conditions including multiple lift-offs, temperatures, or bias fields, to permit averaging of unknown property estimates, as well as to permit estimation of more than one unknown property.

Calibration is further discussed in U.S. patent application Ser. No. 08/702,276 entitled, "Meandering Winding Test Circuit" filed Aug. 23, 1996 by Neil J. Goldfine, David C. Clark, and Homer D. Eckhardt, which issued on Aug. 11, 1998 as U.S. Pat. No. 5,793,206, the entire contents of which are included by reference.

The sensors described below allow for more accurate modeling which enables calibration of the sensor in air, as described above. In each case, a sensing element is provided between each pair of adjacent legs of a meandering drive winding. A sensing element is provided between each pair of adjacent legs in order to assure half wavelength symmetry throughout the array.

Figure 3A:
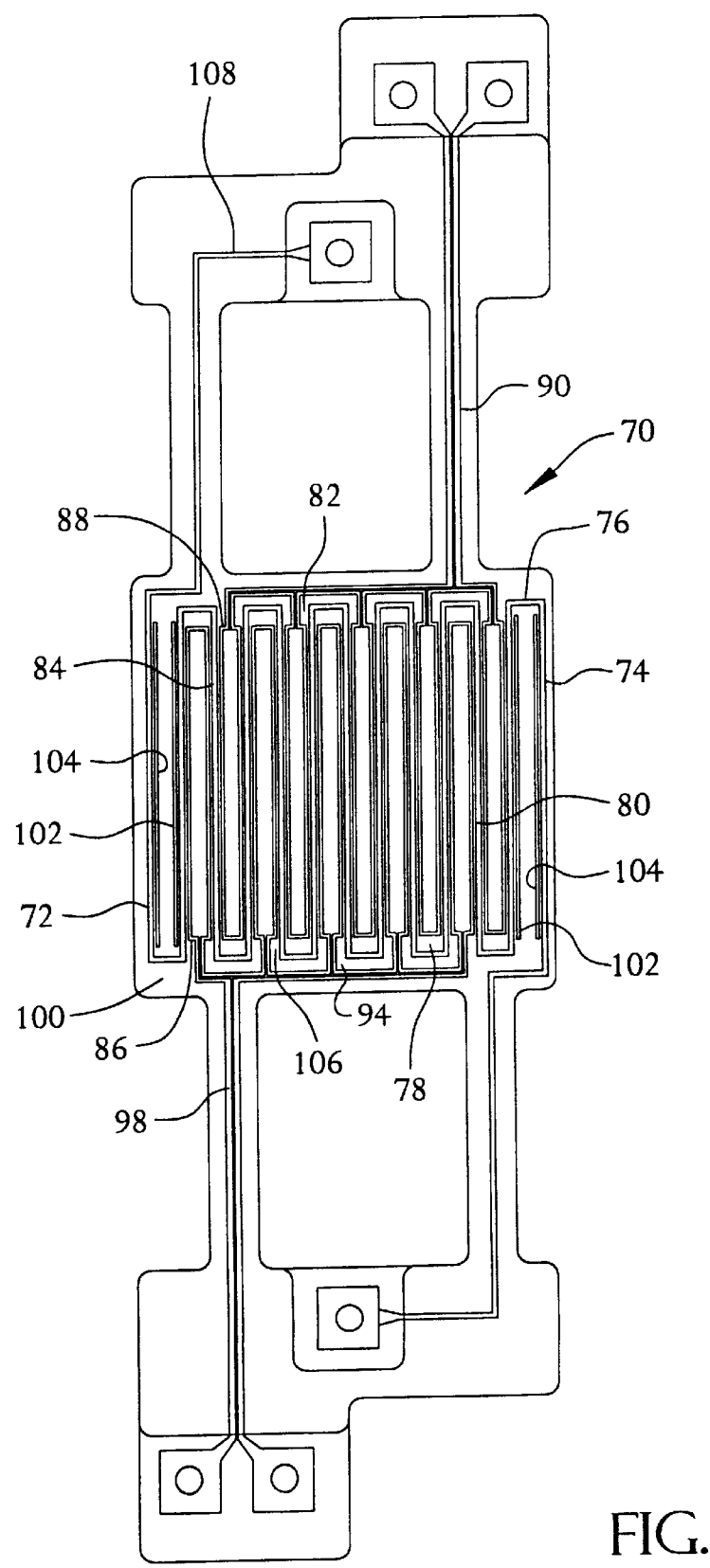
FIG. 3A is a front view of a sensor with a meandering primary winding and a plurality of sensing elements. The sensing elements are connected in two groups. A pair of dummy sensing elements are formed within the final half wavelength of the primary winding.

FIG. 3A shows a sensor 70 having a meandering primary winding 72, also referred to as a meandering drive winding. The primary winding 72 is a square wave having a plurality of parallel legs or extending portion 74 which in FIG. 3A extend vertically. The primary winding 72 has connecting portions 76 which join the extending portions 74 to create the square wave shape.

The alternating of ends that the connection portion 76 extend between to adjacent extending portions 74 form alternating opened channels 78 which alternate opening on one side or the other. The sensor 70 has a plurality of sensing elements 80 located in these channels 78 between two parallel extending portions 74. Each sensing element in the one set 82 of channels, those that are opening to the top in FIG. 3A, has a pair of parallel legs 84 which are adjacent and spaced from the extending portion 74 of the primary winding. The parallel legs are joined by a connecting portion 86 at the closed end of the channel 78 and have a pair of ends 88 extending from the other end, the open end.

The first set 82 of sensing elements 80, the set that opens towards the top in FIG. 3A, are connected in series with their ends 88 connected to a pair of output leads 90 extending away from the array 92, defined by the meandering pattern of the primary winding 72. The sensing elements 80 in the other set 94 of channels 78 those that open towards the bottom in FIG. 3A, are similarly configured with pair ends 81 extending from the bottom open end. The sensing elements 80 of the other set 94 are connected in series with their ends 88 connected to a pair of output leads 98.

The meandering drive winding extends a half wavelength 100 at each end of the array, and a pair of dummy sensing elements 102 and 104 are formed within those final meander half wavelengths to maintain the periodicity of the field as viewed by the end sensing elements. The dummy windings 102 and 104 are not closed and not connected to form a loop so that the net current flowing through the windings is minimized. This simulates the high impedance of the secondary winding terminal connections that minimizes the current flow through the secondary windings. Connecting or shorting the dummy elements together so that they form a closed loop would lead to significant current flowing through the dummy elements which would also perturb the magnetic field distribution and reduce the effectiveness of the dummy elements in maintaining the periodicity of the field distribution. The dummy elements are introduced to expose the end secondary elements to the same magnetic field distribution as the interior secondary elements. The array could be similarly extended even further if required for accurate modeling. The purpose is to extend the periodicity of the field beyond the last connected sensing element to reduce the unmodeled "edge" effects at the end of the sensor.

The ends 88 of the sensing elements are set back from the connecting portions 76 of the meandering winding. However, it has been found that a setback of at least one wavelength, as previously believed, is not required. A setback of one quarter to one half wavelength has been found sufficient to assure that the magnetic flux linked by the connecting elements is less than 10 percent of the total flux linked into the sensing elements. The greater the setback, the smaller the amount of linkage and the more the extended portions appear to be infinite to the sensing elements. Too much setback win reduce the total signal size which is determined by the area of the sensing element footprint.

At the ends of the sensing elements which connect to the respective leads 90 and 98, the etched leads are shouldered in, as at 106, to minimize the coupling of the leads 90 and 98 extending from the sensing elements 80 with the meandering primary or drive winding 72. The leads in the region of the primary winding 72 are exposed to stray, fringing magnetic fields. The fields at the edges of the main footprint of the sensor are not represented in the continuum model for the response of the sensor. The response to these stray fields must either be minimized, such as by reducing the gap between the secondary leads as discussed above or by compensated for the effects through an equivalent circuit or calibration as discussed below. Bringing element leads out close together or in twisted pairs is a standard method for eddy current sensors. The goal is to link fields only in the desired sensing regions within the footprint. The primary winding 72 has a pair of leads 108.

The sensor 70 shown in FIG. 3A is enlarged for clarification. The actual sensor 70 typically has a primary winding having a length of the extending portion 74 of approximately three-quarters of an inch In this embodiment, a width of the sensor is approximately the same.

Figure 3B:
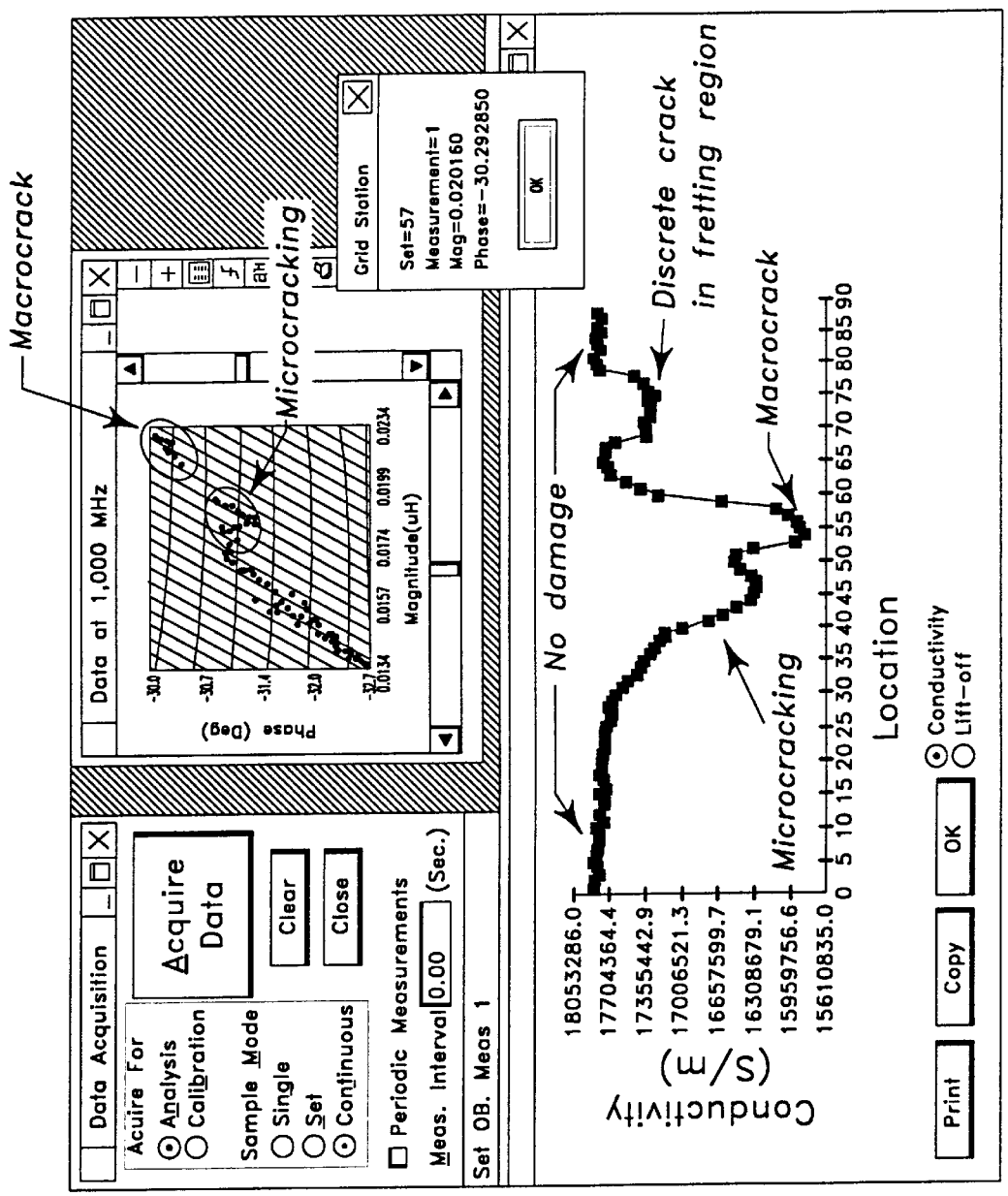
FIG. 3B is a scan across a fatigued part using the sensor of FIG. 3A.

FIG. 3B shows a scan across a 4-pt. bending fatigue specimen using the sensor 70 described in FIG. 3A. The response to the discrete crack in the fretting region illustrates the fact that a crack gives the same response at any location within a group of sensing elements.

Figure 4:
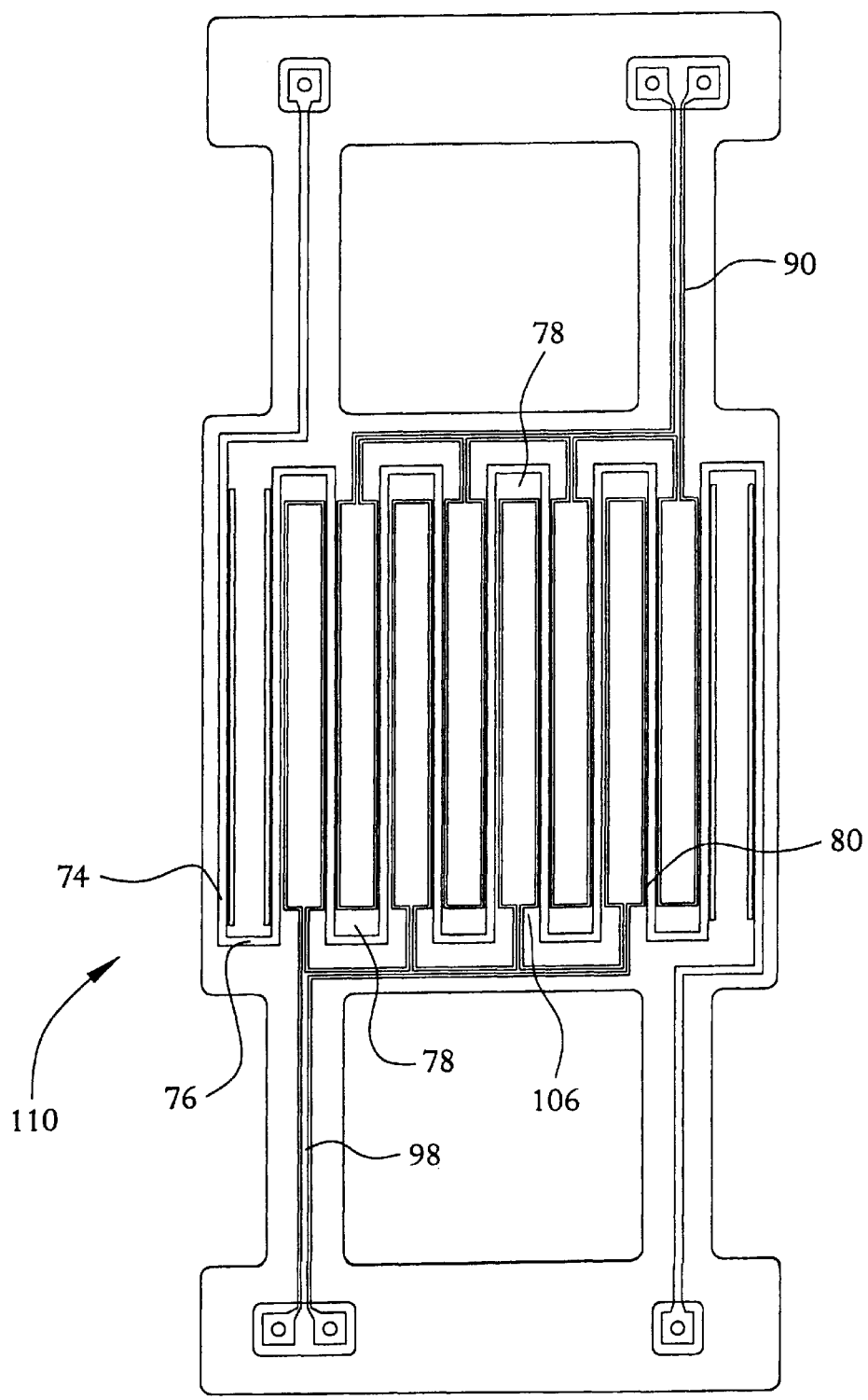
FIG. 4 is a sensor similar to that shown in FIG. 3A wherein each grouping has four sensing elements, in contrast to each having five sensing elements.

FIG. 4 shows an alternative embodiment of a sensor 110. In a preferred embodiment of the sensor 110 is the length of the extended portion 74 of the primary winding 72 is approximately an inch and one-half. The width of the sensor is approximately the same. The distinction between the sensor 70 in FIG. 3A and the sensor 110 in FIG. 4 is that FIG. 3 illustrates two groupings, each of five sensing elements 80; whereas, FIG. 4 illustrates two groupings, those sensing elements on the channels 78 opening up and those sensing elements in the channels 78 opening down as seen in the figures, each of four sensing elements.

Figure 5:
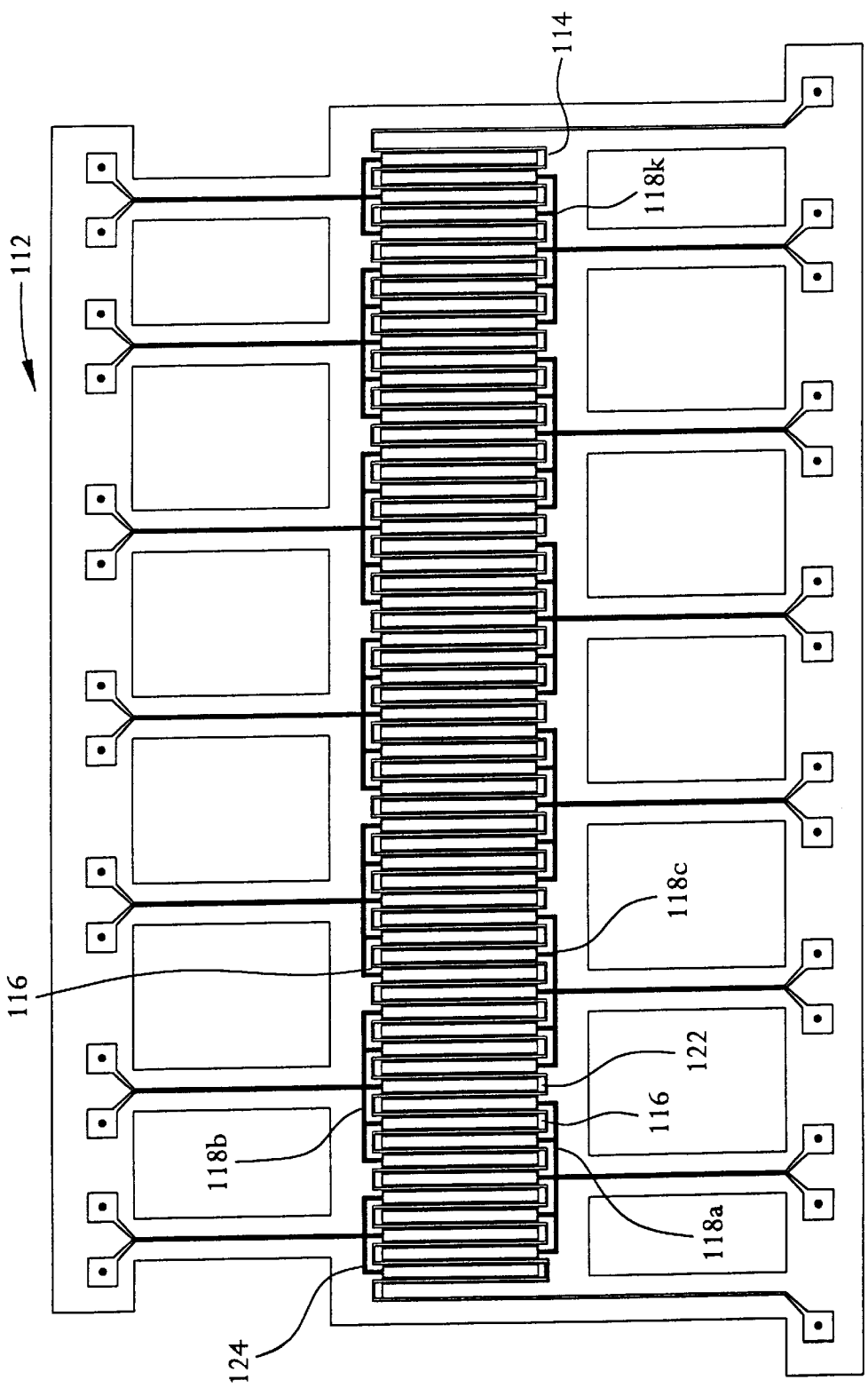
FIG. 5 illustrates a sensor having a meandering primary winding with eleven (11) groups of sensing elements. The sensing elements on one side are overlapped/intertwined with sensing elements of two groups of the other side.

FIG. 5 illustrates a sensor 112 having a primary winding 114 and a plurality of sensing elements 116. In contrast to the previous embodiment, in which the sensing elements are in two groups, the sensing elements 116 are in eleven (11) groupings 118, each of five sensing elements 116. Sensing elements 116 are grouped to cover a desired area as a pixel, and pixels are then overlapped to build an image in one dimension (e.g., Group 118b has five sensing elements 116. The center element 122 is interposed between the end elements 116 of group 118a and 118c, wherein the two elements on one side, the left side in FIG. 5, are interposed between elements of group 118a and the other two elements are interposed between elements of group 118c. ) A pixel is an area defined by the sensor elements. The grouping, comparing, and differentiation of sensor elements effects the pixel size. FIG. 5 also includes two additional groups 124, each of three sensing elements 116. These groups 124 are at the edges of the sensor 112 and can be used to detect the edge of a material under test when in scan mode.

Figure 6:
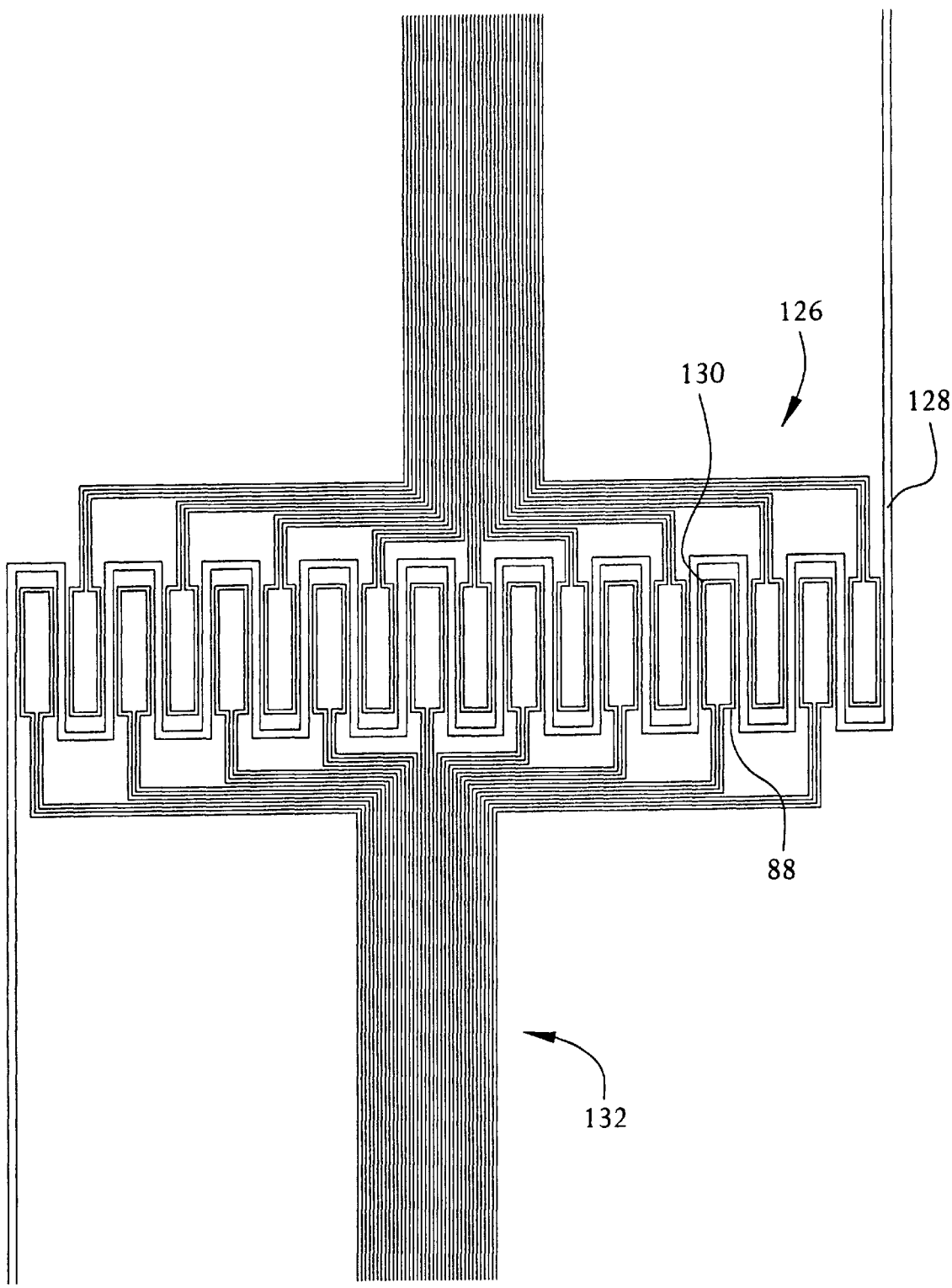
FIG. 6 is a front view of a sensor with a meandering primary winding and having a plurality of sensing elements which each have their own individual leads.

FIG. 6 illustrates a sensor 126 having a primary winding 128 and an array of 18 sensing elements 130, none of which are grouped. Similar to the previous embodiments, the ends 88 of the sensing elements are shouldered in to minimize coupling of the leads 132 with the primary winding 128.

Figure 7:
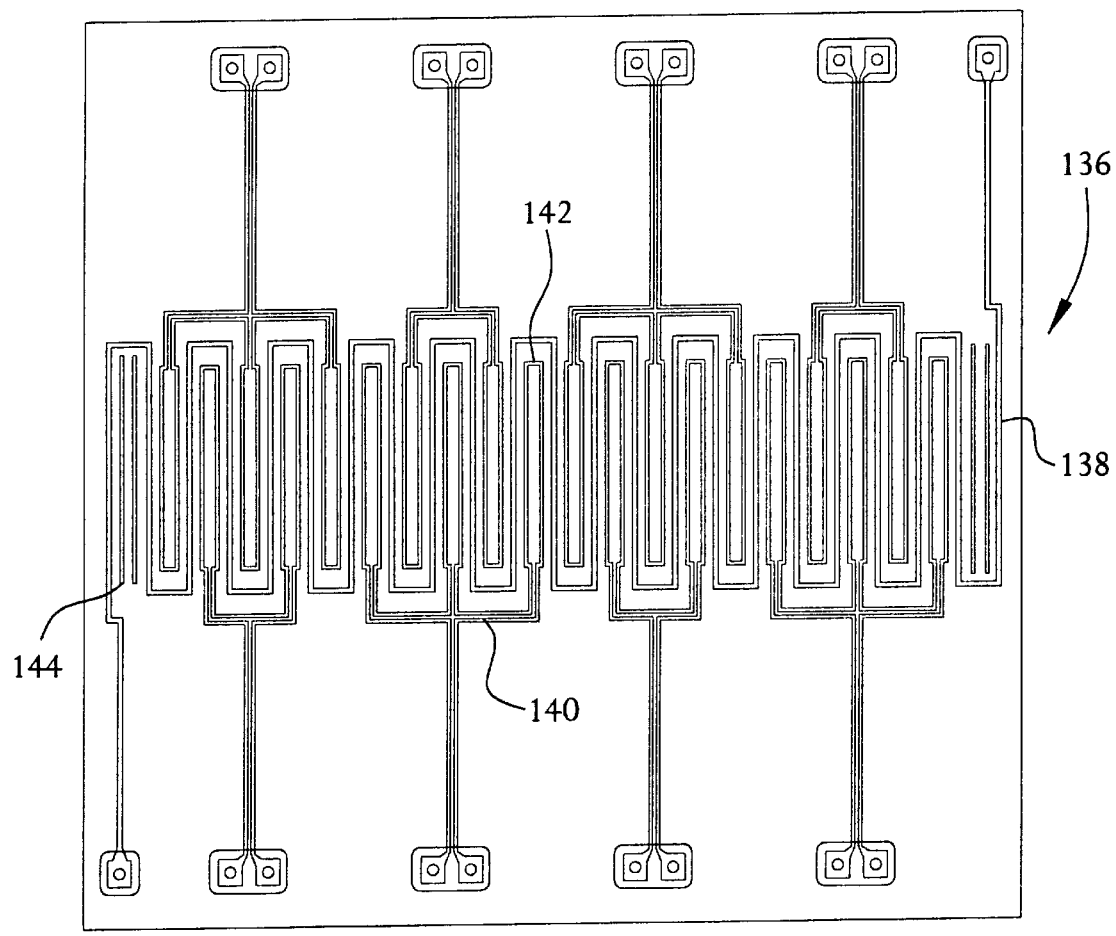
FIG. 7 is a front view of a sensor with a meandering primary winding and having a sensing elements grouped into groups of two or three individual sensing, secondary, elements which are not overlapped.

FIG. 7 illustrates a sensor 136 having a primary winding 138 and eight groupings 140 of secondary elements 142, containing either two or three individual secondary elements 142. By combining the signals from a two-element and three-element group on either side of the primary winding, an imaging pixel is created. The sensor 136 of FIG. 7 is a non-overlapping grouping array in contrast to the sensor 112 of FIG. 5 which is an overlapping grouping array. The array of FIG. 7 then provides a four-pixel array that can be scanned across the material under test to provide an image of the material properties. In this array the gap between the secondary leads and the primary windings is increased to reduce the coupling of higher order spatial modes of the magnetic flux into the secondary windings, as discussed below. The sensor 136 has dummy sensor elements 144 similar to FIGS. 3 and 4.

Figure 8:
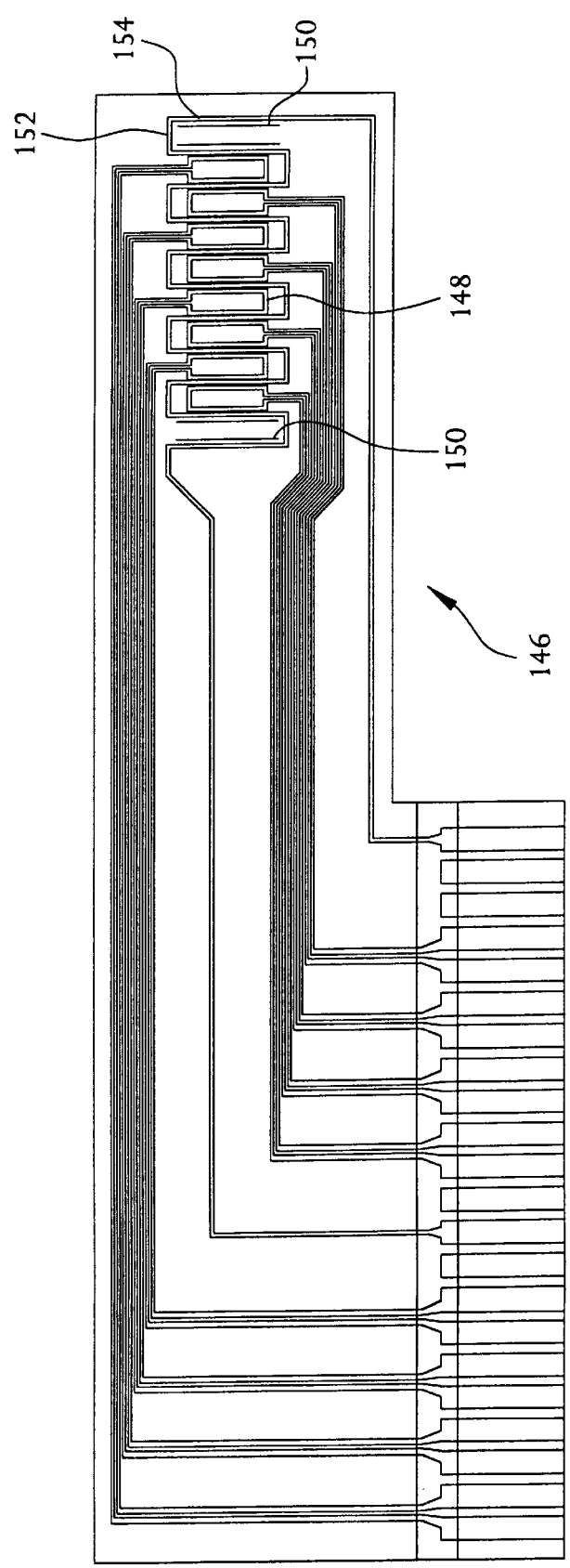
FIG. 8 is a front view of an alternative sensing element and meandering primary winding having a secondary array with connections to each individual secondary array.

FIG. 8 is an expanded version of a sensor 146 having an eight element array 148. Connections are made to each of the individual secondary elements 148. Dummy elements 150 are added, the secondaries are set-back from the connecting portion 152 of the primary winding 154 and the gap between the leads to the secondary elements are minimized. In a preferred embodiment, the dummy elements have a length of 3.0 mm and a width of 0.083 mm The parallel legs or extending portion of the primary winding have a length of 3.2 mm and a width of 0.167 mm. The set-back distance is 0.5 mm and the secondary elements are 2.2 mm in length. The primary to secondary gap separation is 0.083 mm The wavelength $\lambda$ is 2 mm In addition to improvements in the sensors as explained above, other improvements such as in the instrumentation described in FIG. 1 improves the correlation of the measurements received through the instrumentation to the actual properties of the material under test.

Figure 9:
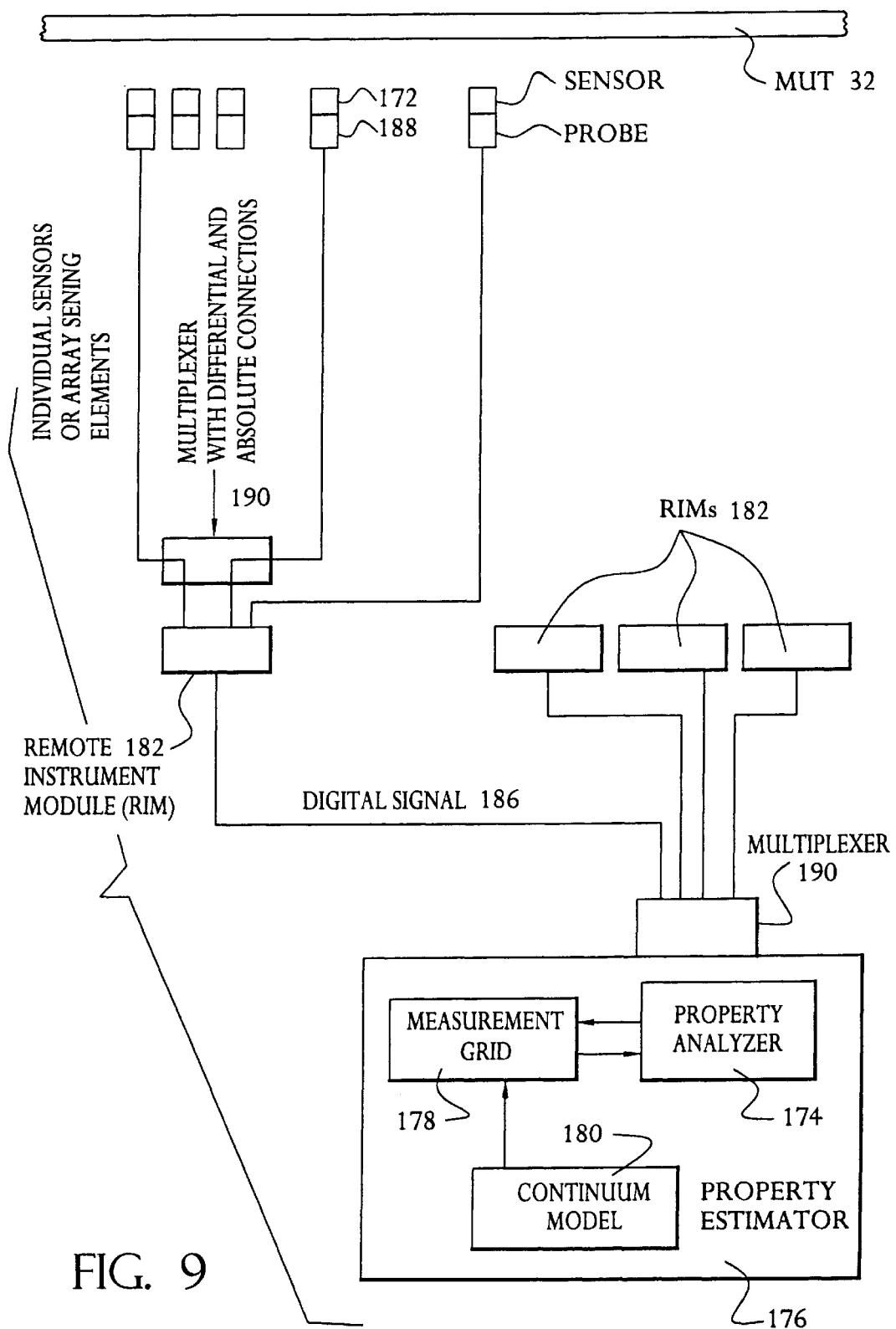
FIG. 9 is a flowchart of an alternative embodiment of the instrument and a material under test. The instrument includes a multiplexer near the sensors that provide both differential and absolute connections of the sensing elements for an array.

FIG. 9 illustrates an alternative embodiment of the instrumentation 170. Similar to FIG. 1, the sensor 172 is placed in proximity to the material under test 32 and receives an input current or voltage source. The sensing elements as described above in FIGS. 3 through 8 are measured to determine the voltage induced in the respective sensors. This magnitude and phase is sent into a property analyzer 174 and upon comparison an estimate of the material test properties are determined. In FIG. 9, the instrument 170 has a property estimator 176, in a preferred embodiment, a microprocessor, which contains in software and data the property analyzer 174, measurement grids 178, and a continuum model 180 that generates the measurement grids off-line and stores them in a measurement grid library for use on-line. The property estimator 176 is connected to a remote instrument module 182 (RIM) which contains the analog portion of the impedance analyzer 184. The signal from the RIM 182 to the property estimator 176 is a digital signal 186 to minimize interference shielding issues and drop-in signal issues. From the RIM 182, the sensor 172 is connected through a probe 188. In a preferred embodiment the probe contains additional circuitry to provide both multiplexing of multiple sensing elements and additional signal amplification as described below with respect to FIGS. 10A and 10B .

In a preferred embodiment both the property estimator and the RIM can have multiplexers 190 so that each can have multiple items which are fed from them, i.e. the property estimator 176 may have multiple RIM 182 and each RIM 182 may have multiple sensors. The wiring and shielding near the sensor head is fixed rigidly to limit changes after initial calibration.

Figure 10A:
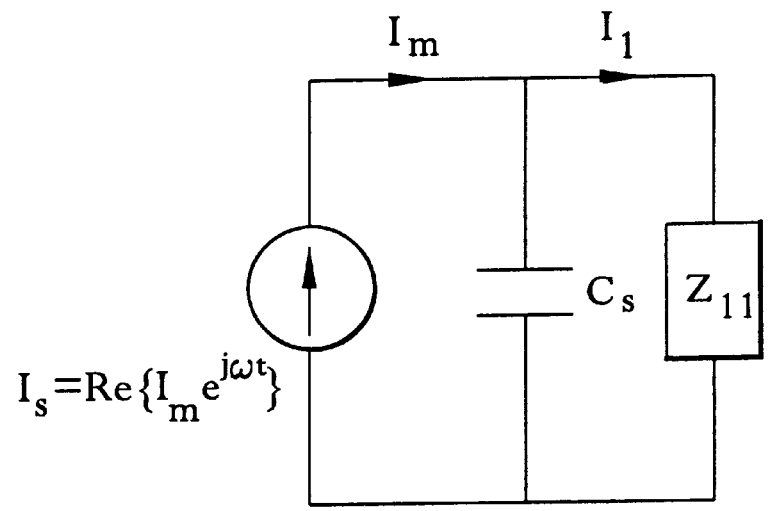
FIG. 10A is a schematic of a circuit for the sensor primary winding for use in modeling to compensate for cable loading effects.
Figure 10B:
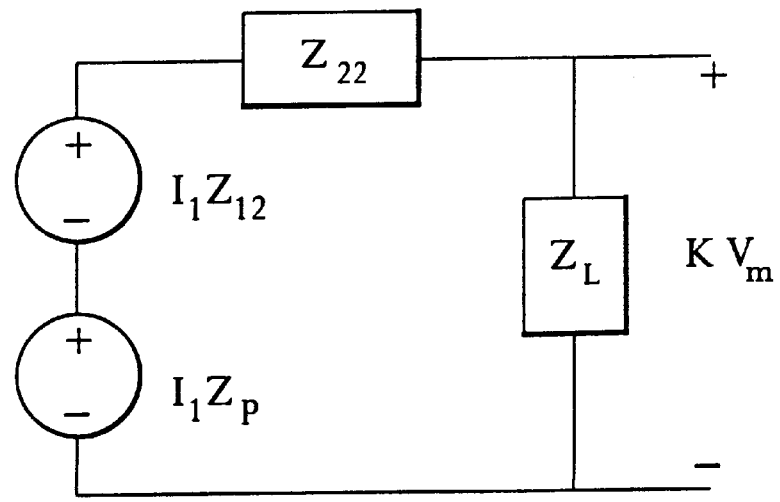
FIG. 10B is a schematic of a circuit for the sensor secondary winding for use in modeling to compensate for parasitic and cable loading effects.

FIGS. 10A and 10B illustrate equivalent circuits for the sensor response including parasitic and stray effects of the sensor placement inside the probe and the connection cables. FIG. 10A illustrates a sinusoidally time-varying current Is having a complex amplitude Im is input to the primary winding of the sensor and an output voltage of complex amplitude $V_m$, as illustrated in FIG. 10B, is measured across the secondary elements. This gives the measured transimpedance between the primary and the secondary as $Z_m = V_m / I_m$. The complex scale factor K is introduced as a scaling parameter, determined from calibration, which accounts for variations or drift in the response of the electronic components. The resulting corrected transimpedance is then $Z_{corrected} = K Z_m$. The response of the sensor, represented by the transimpedance $Z_{12}$, the primary self-impedance $Z_{11}$, and the secondary self-impedance $Z_{22}$, can be derived from continuum models that account for the material geometric properties of the sensor and surrounding media. The corrected transimpedance can differ from the transimpedance calculated from the model because of unmodeled effects, such as the capacitive loading of the cable connecting to the source primary winding (Cs), stray or parasitic coupling from the primary to the secondary ($Z_p$), and loading of the secondary windings through an impedance ($Z_L$). In the simplest case, this load impedance can be represented with a cable capacitance in parallel with an instrument load resistance. Due to the loading of the cable on the input side, the effective current into the sensor has complex amplitude $I_1$.

To obtain absolute measurements of the material properties, several approaches can be used. In the first approach, one simply measures the response of the sensor in air. Using the relation $Z_{12}=KZ_m$ then allows the scale factor K to be calculated. This factor of K is then used in subsequent measurements to the corrected value of the transimpedance, related to the measured transimpedance through $$Z_{corrected}=KZ_m=Z_{12} \quad (1)$$

is taken to be equivalent to the ideal transimpedance calculated from the model $Z_{12}$. In reference to FIG. 10B, the elements $Z_p=0$ and the other loading effects are assumed to be negligible ($C_s=0, Y_L=1/Z_L=0$). Although this one point calibration is adequate for some measurements, it does not account for the parasitic impedances inside the sensor itself.

The second approach uses a two point calibration sequence to set the calibration values for both the scale factor K and the parasitic impedance $Z_p$. In this case, the first step involves measuring the transimpedance for a shunt sensor, which as the secondary winding leads cut and shorted together, so that the measured response gives the parasitic impedance ($Z_p=Z_m$). In reference to FIG. 10B, the elements $Z_{12}=Z_{22}=0$ and the other loading effects are negligible ($C_s=0, Y_L=1/Z_L=0$). The second step then requires replacing the sensor tip and measuring the response of the sensor in air. Equating the corrected impedance with the ideal transimpedance calculated from the model then allows the scale factor K to be calculated using the relation.

$$Z_{corrected}=KZ_m-Z_p=Z_{12} \quad (2)$$

In subsequent measurements on the test materials, the measured transimpedance $Z_m$ is converted into a corrected transimpedance using Equation (2) and the calibration values for K and $Z_p$. While this approach is more accurate than the first approach, it does not properly account for other factors that can influence the response of the measurement, such as the properties of the connector cables.

The third approach also uses a two point calibration sequence to set the calibration values for both the scale factor K and the parasitic impedance $Z_p$ but also accounts for the cable and instrumentation loading effects on the response. In this case the equivalent circuit for the response is shown in FIG. 10B. The corrected transimpedance is then related to the measured transimpedance and the expected sensor transimpedance $Z_{12}$ through $$Z_{corrected} = KZ_m = \frac{KV_m}{I_m} = (Z_{12}+Z_p)\frac{1}{1+j\omega C_s Z_{11}}\frac{Z_L}{Z_L+Z_{22}} \quad (3)$$

with ω the angular frequency of the excitation and j the square root of −1. It is clear that Equations (1) and (2) are special cases of Equation (3). The first step of the calibration involves measuring the transimpedance for a shunt sensor, which has the secondary winding leads cut and shorted together. Using known values for the cable capacitances, nominally 20 pF/ft, a fixed instrumentation load resistance of 20 kohms, and the model response for the sensor in air for the expected primary self-impedance $Z_{22}$, equation (3) then gives the parasitic impedance as $$Z_p=KZ_{m,shunt}(1+j\omega C_s Z_{11}) \quad (4)$$

Similarly the second step involves replacing the sensor and measuring the response in air. Using the known information from the shunt measurement and the model response for the sensor in air for the expected sensor impedances $Z_{12}$ and $Z_{22}$, Equation (3) then gives the scale factor as $$K = \frac{(Z_{12}+Z_p)}{Z_{m,air}}\frac{1}{1+j\omega C_s Z_{11}}\frac{Z_L}{Z_L+Z_{22}} \quad (5)$$

Equations (4) and (5) then form a set of two equations with two complex unknowns, K and $Z_p$. These can be solved to give the calibration factors as $$K = \frac{Z_{12}\dfrac{1}{1+j\omega C_s Z_{11}}}{Z_{m,air}\dfrac{Z_L+Z_{22}}{Z_L} - Z_{m,shunt}} \quad (6)$$

$$Z_p = \frac{Z_{12}Z_{m,shunt}}{Z_{m,air}\dfrac{Z_L+Z_{22}}{Z_L} - Z_{m,shunt}} \quad (7)$$

The scale factor K generally has a magnitude of approximately one, with a phase near zero degrees, while the parasitic impedance $Z_p$ generally has a magnitude that is small compared to $Z_{12}$. In practice it is usually sufficient to use Equation (4) to determine the parasitic impedance, assuming that K is equal to one, and then use Equation (5) to determine the value for the scale factor K. In either case, the calibration factors are used with Equation (3) to determine the corrected transimpedance during measurements on materials with unknown properties that are to be determined. A least-squares minimization routine or a table lookup routine that relates the material properties to the sensor impedances $Z_{11}$, $Z_{12}$, and $Z_{22}$ can then be used to solve the reverse problem of determining the material properties from the corrected impedance. For example, a simple iterative approach would take the measured impedance of the sensor when it is in close proximity to the material under test and convert this to an expected sensor transimpedance $Z_{12}$ using Equation (3) and values for the self-impedance of the sensor in air. Using a table look-up routine, the material properties can be obtained from $Z_{12}$ and the self-impedances $Z_{11}$, and $Z_{22}$ can be calculated using these new properties. An updated transimpedance and material properties can then be obtained as well. Since the cable and loading corrections to the transimpedance are generally small, this iterative process an converge to the correct material properties.

This approach can also be applied to improve the sensitivity of the sensor if a reference part calibration is allowable in the application. As an example, one can calibrate on flat reference parts before performing measurements on curved test materials. With the input current amplitude and output voltage levels independently adjustable in the instrumentation electronics, the sensitivity of the sensor can be increased to span the range of the material properties in the reference calibration. In this case measurements are performed over two conditions, such as two lift-off heights on a given piece of material, and then the scale factor K and the parasitic impedance are calculated. For a multiple frequency measurement this procedure is performed at each frequency.

Each successive approach illustrates a refinement in the measurement technique that allows that absolute property measurements to be determined. In some situations, additional circuit elements may be required to compensate for the undesired effects in the measurement response. These could include, but are not limited to, adding additional elements to represent the inductive and resistive losses of the cables and sensor lead wires to match the response of the sensor over the frequencies of interest. For example, the illustration of FIG. 10A indicates that the cable effects can be modeled as a single lump capacitance. One can also include the lumped elements for the series inductance and resistance of the cable or, particulary at the higher frequencies, a transmission line or a distributed network of elements.

Another key aspect of this invention that allows for absolute property measurements is the placement of the critical instrumentation electronics as close as possible to the sensor head with extra fixturing and molded structures that rigidly hold the shielding and wiring in place. This prevents movement of the shielding and wiring after calibration, which reduces unmodeled changes in the sensor behavior. The portion of the electrical instrumentation placed in the head of the probe involves a high-speed (video) operational-amplifier used for making a differential measurement of the input signal. The gain of the operational amplifier can be adjusted, nominally over a range of 30–3000, so that the amplitude of the output voltage from the probe can be kept essentially constant as the frequency is varied. Prior to this change, the sensor was much more sensitive to cable effects, such as the orientation and placement of the cable, because at the lower frequencies the shielding becomes less effective as the fringing electromagnetic fields beyond the shielding become more significant. This led to a decrease in sensitivity to the material under test and an increase in the magnitude of the parasitic impedance.

Figure 11A:
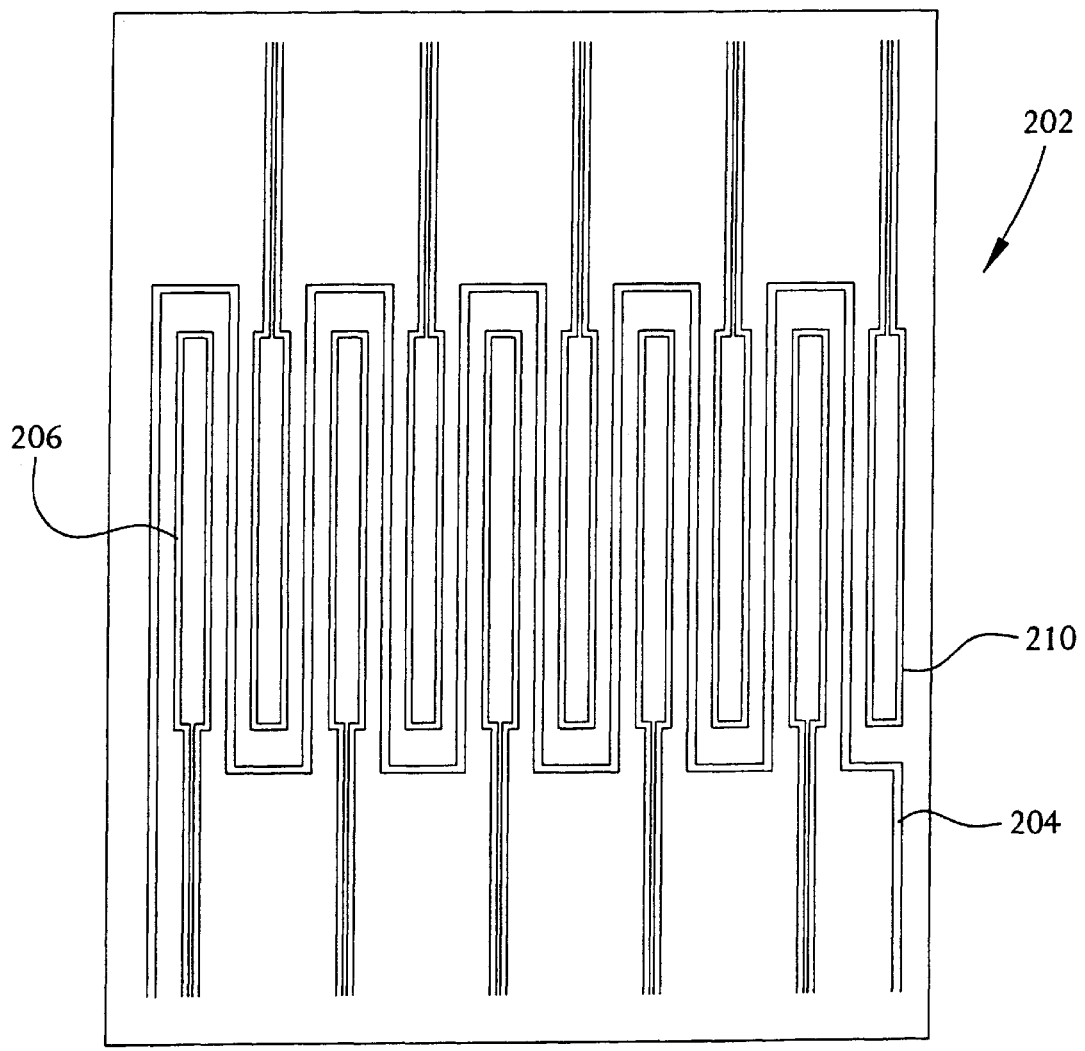
FIG. 11A is a schematic top view of a sensor with all sensing elements connected individually.

FIG. 11A illustrates a sensor 202 having a primary winding 204 and a plurality of sensing elements 206. The sensing elements 206 have their individual output leads 208. A sensing element 210 of the sensing elements 206 is located outside the area defined by the primary winding 204. This sensing element 210 outside the primary winding 204 supports concatenation of this fixed length sensor 202 with other sensor array modules to form a longer continuous array.

Figure 11B:
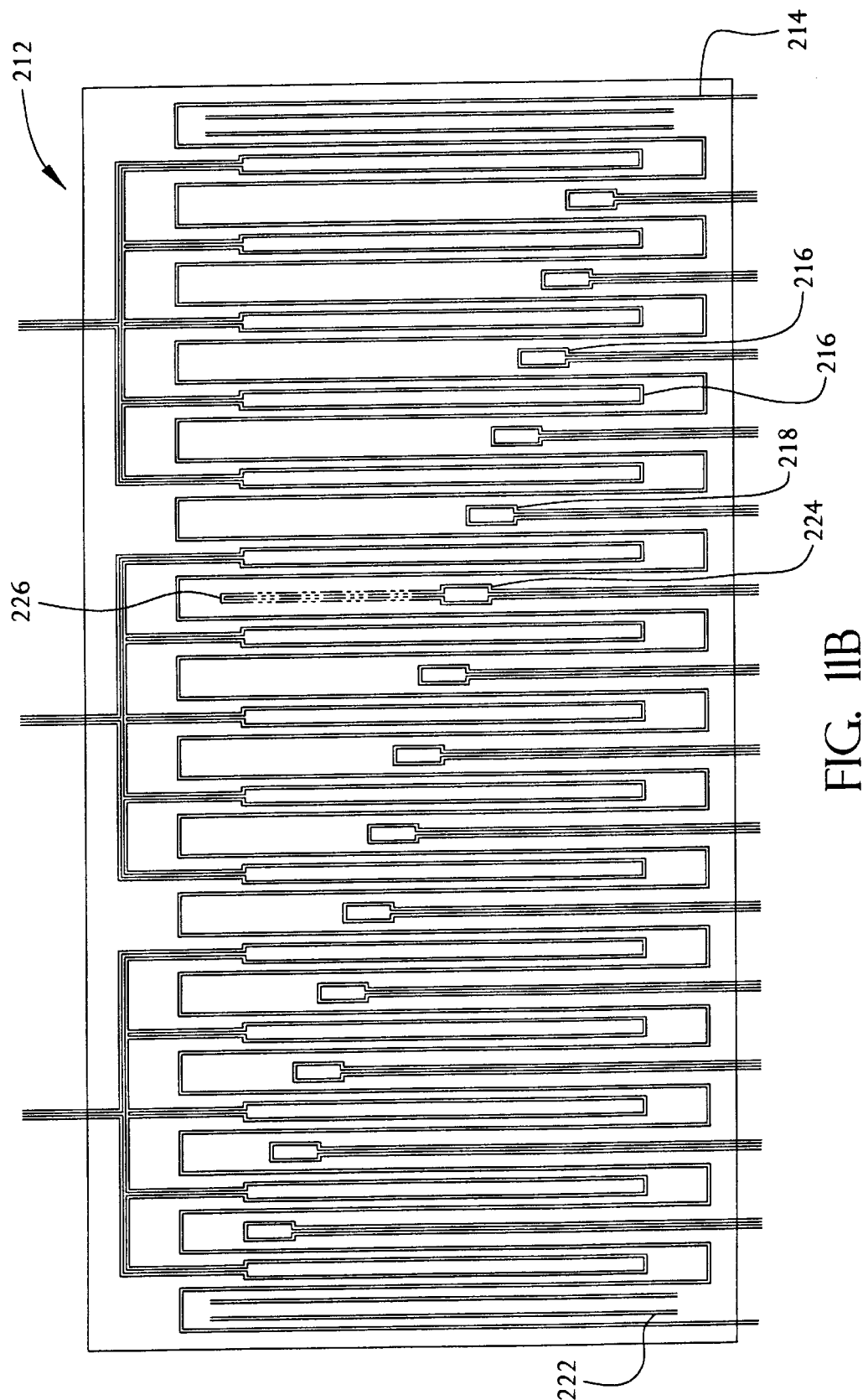
FIG. 11B is a schematic top view of a sensor with offset sensing element on one side connected individually. The elements on the opposite side of the meandering primary are grouped or connected individually.

FIG. 11B illustrates a sensor 212 having a primary winding 214 and a plurality of sensing elements 216. The sensing elements 218 of the sensing elements 216 on one side, those in the channels opening to the bottom of FIG. 11B, are smaller sensing elements. These sensing elements 218 are offset, starting at the top on the left in FIG. 11B. The offset is perpendicular to the scan direction to support image building of the abnormal "crack" imaging. The elements 218 on the opposite side of the meandering are shown grouped. It is recognized that the elements can also be connected individually, if desired.

The sensor 212 has dummy sensor elements 222 similar to FIGS. 3, 4, and 7. A sensing element 224 is shown with an elongated vertical segment 226, in phantom, covering the entire sensor height. Such an elongated segment used on each sensing element would result in equal coupling areas for each individual sensing element permitting improved tuning of electronics when switching (multiplexing) between elements.

Referring back to FIG. 7, the sensor 136 has another feature not discussed above. The primary winding 138 of the sensors meander in a scroll wave pattern. The sensor 136 has sensing or secondary elements 142 interposed between the extending portions 74 of the primary winding 138. Similar to FIG. 4, the sensing elements 142 in FIG. 7 are set in groups containing either two or three individual sensing elements 142. In contrast to the sensor 110 designs shown in FIG. 4, the secondary elements 142 are moved farther away from the primary winding 138 along the long parallel lengths of the sensor. The optimal spacing will depend on the noise level of the instrument.

Figure 17:
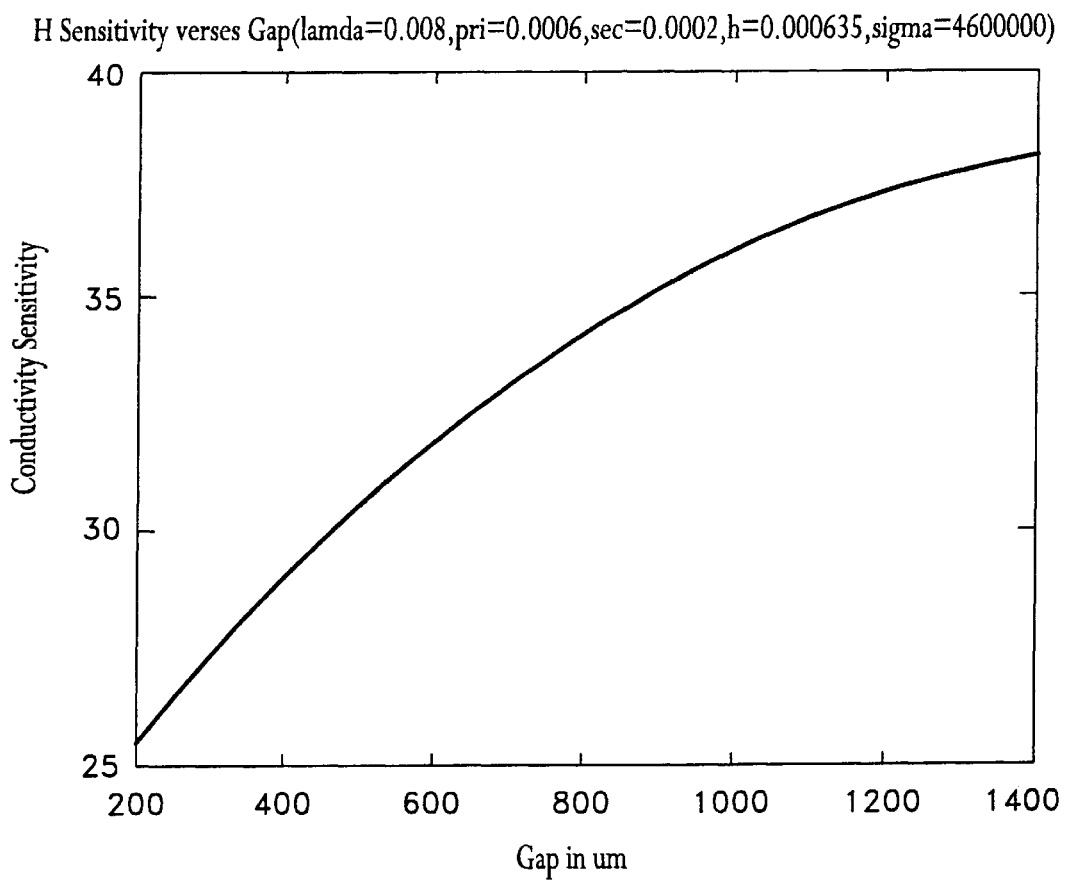
FIG. 17 is a graph of conductivity sensitivity versus gap for the parameters listed on the graph.
Figure 18:
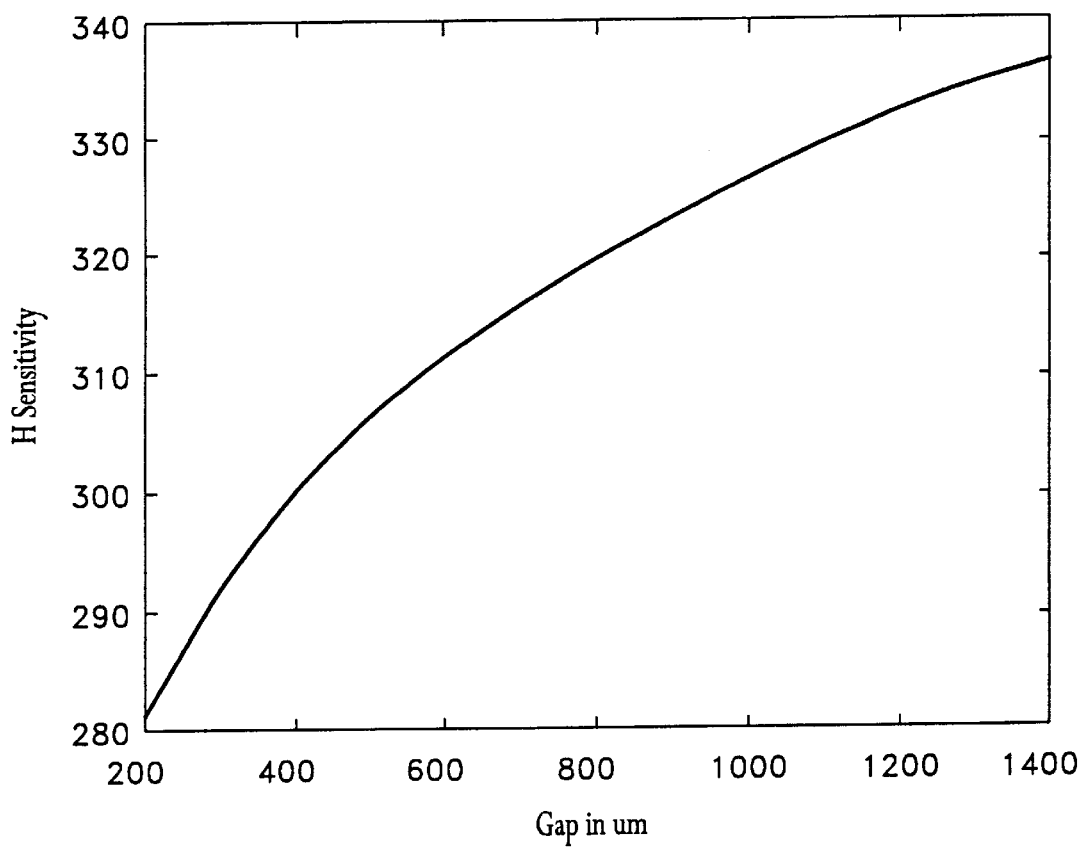
FIG. 18 is a graph of H sensitivity versus gap for the parameters listed on the graph.
Figure 19:
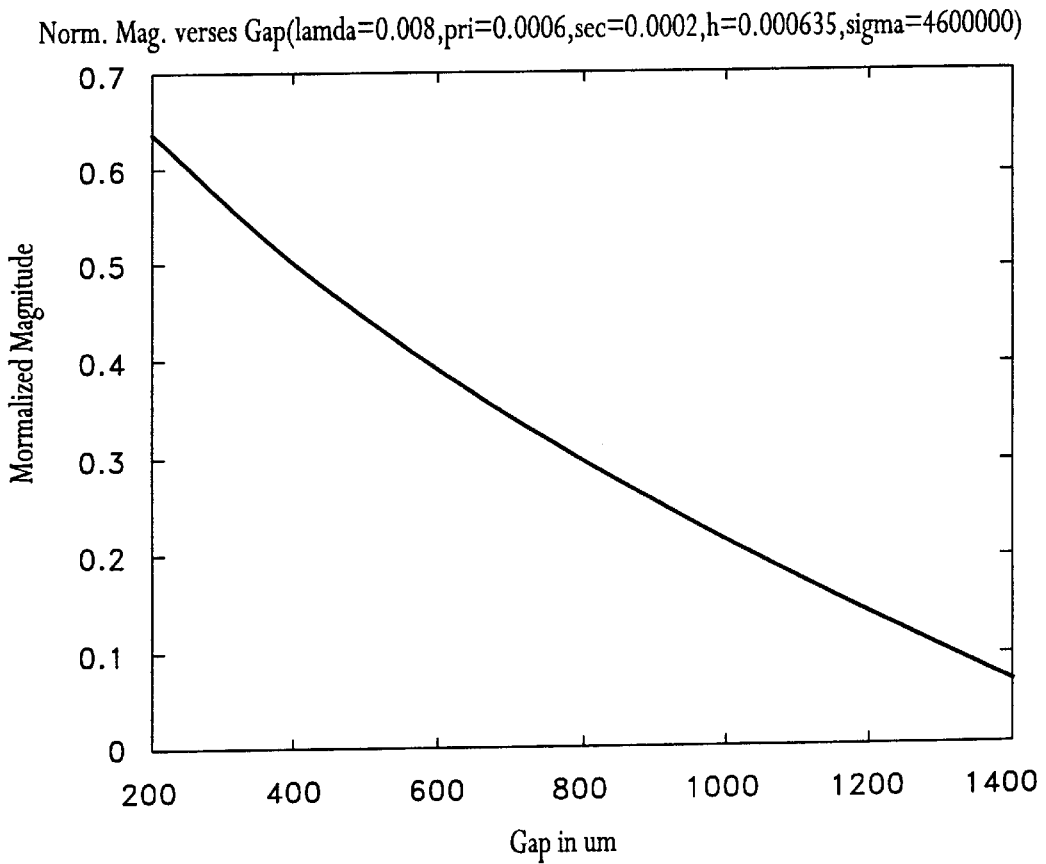
FIG. 19 is a graph of Normalized Magnitude versus gap for the parameters listed on the graph.

As shown in FIGS. 17 and 18, the larger the gap between the primary and the secondary sensing elements, the higher the sensitivity for conductivity or liftoff, or other properties of interest. However, making the gap larger will reduce the signal to noise ratio. Thus, optimal gap size will depend on the noise level and sensitivity requirements.

Increasing the gap between the secondary and primary windings has the effect of reducing the coupling to higher order spatial modes. It follows that the sensor then responds predominantly to the lower order spatial modes, which have a deeper depth of penetration into the material under test, so that the sensor is more sensitive to subsurface properties of the material under test.

Figure 22C:
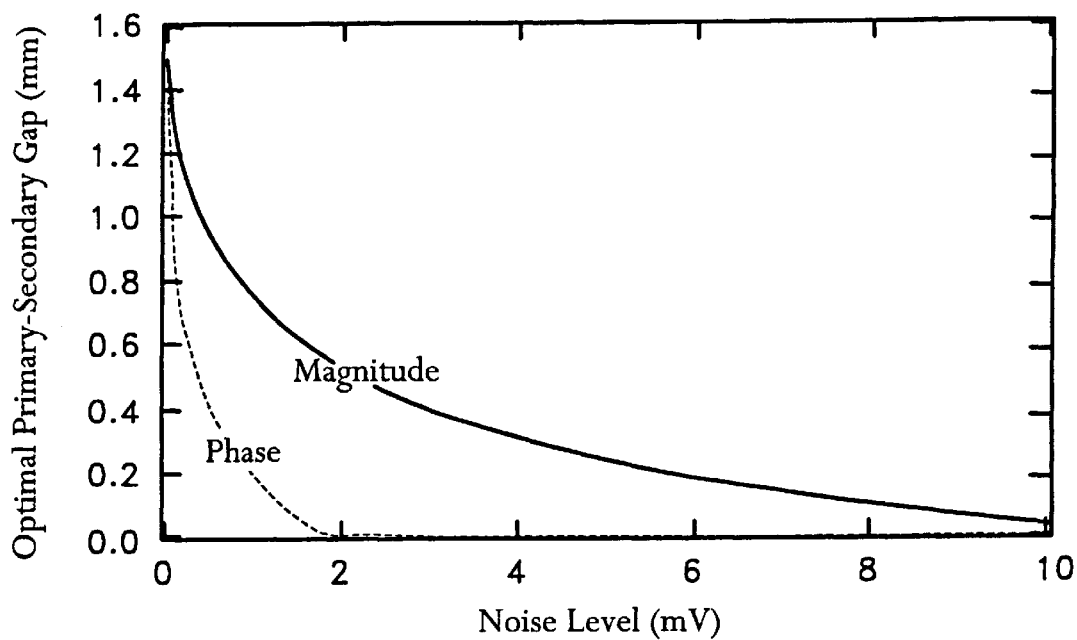
FIG. 22C is a plot of the optimum primary to secondary distance as the noise level of the measurement is varied.
Figure 22A:
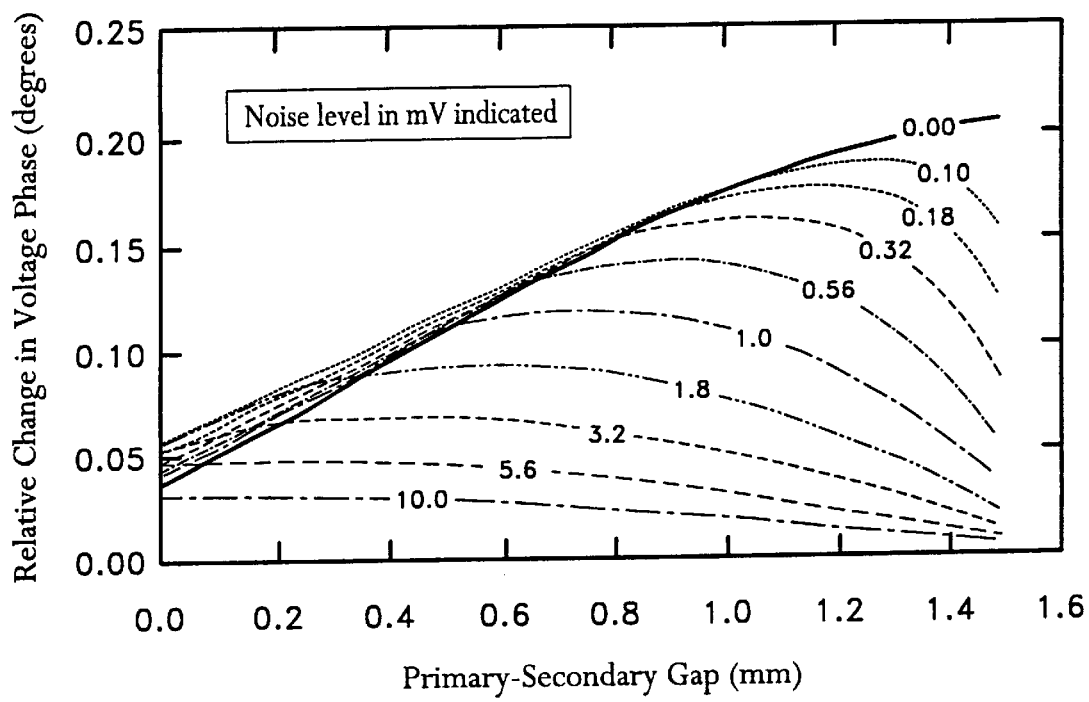
FIG. 22A is a plot of the relative change in the magnitude of the voltage signal as the primary to secondary distance and noise level in the measurement are varied.
Figure 22B:
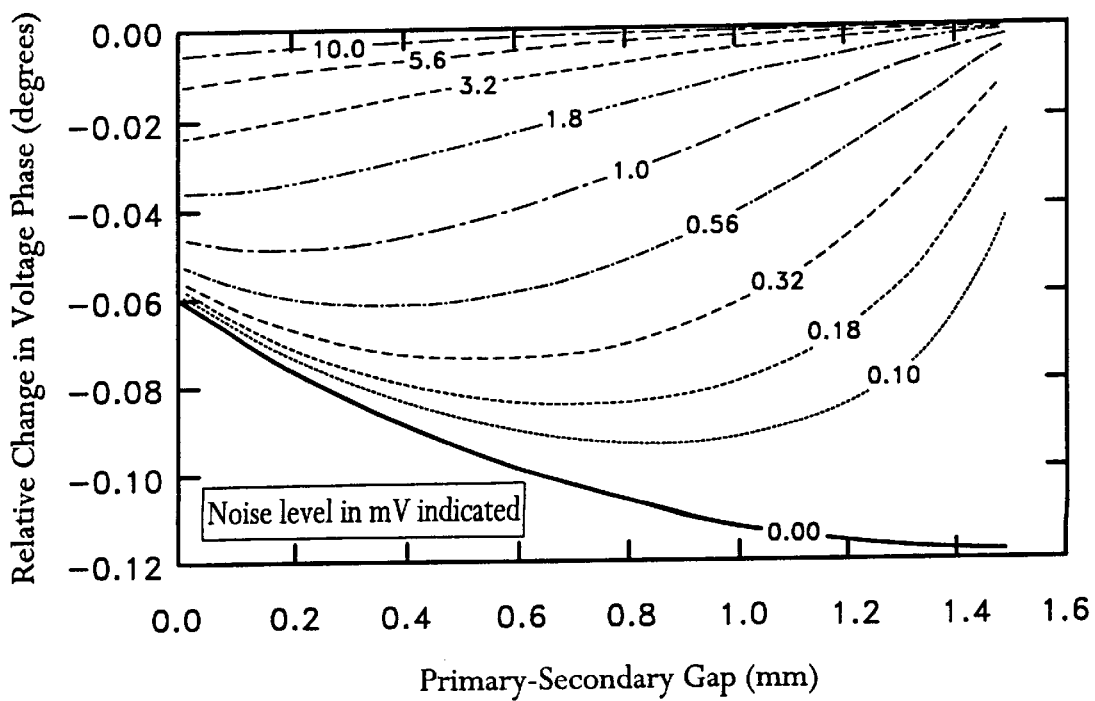
FIG. 22B is a plot of the relative change in the phase of the voltage signal as the primary to secondary distance and noise level in the measurement are varied.

To illustrate the enhancement in sensitivity to subsurface material properties by increasing the secondary to primary gap, consider the plots shown in FIGS. 22A, 22B, and 22C. These plots were generated for a stratified media above the sensor consisting of a 60 μm insulating layer, a 1016 μm metal layer having a base conductivity of 1.74E7 S/m, a 25.4 μm insulating layer, a second metal layer consisting of 508 μm of reduced conductivity (1.653E7 S/m) and 508 μm of the base conductivity, and a final insulating layer. The region of reduced conductivity in the second metallic layer represents damage, for example, by corrosion or cracking, that could compromise the integrity of the structure. To show the sensitivity of the sensor response to the damage region, the secondary to primary gap G was varied while holding the remaining sensor dimensions constant. The range in G can be expressed by $$0 < G < \frac{\lambda}{4} D \frac{C}{2} \tag{8}$$

where λ is the spatial wavelength, D is the width of the secondary winding, and C is the width of the primary winding. These calculations assumed an 8 mm wavelength sensor having a primary width of 0.6mm and a secondary width of 0.2 mm so that the maximum value for G is 1.5 mm. Assuming a current amplitude of 1A and a temporal excitation frequency of 15.8 kHz, the sensitivity of the sensor given by the relative change in the sensor voltage between damaged and undamaged materials can be expressed as $$\Delta V = \frac{V_{damaged} + V_{noise}}{V_{undamaged} + V_{noise}} \tag{9}$$

where $V_{noise}$ is the combined noise level of the instrumentation, cables, and any other uncorrelated noise sources.

As shown in FIGS. 22A and 22B, the change in the magnitude and phase of the voltage increases monotonically with the primary to secondary gap distance in the absence of measurement noise so that the noise level is zero. This indicates that the sensor is most sensitive to the subsurface change in conductivity when the secondary elements are as close together as possible and is consistent with coupling of the lowest order spatial modes of the magnetic field. In real measurements the noise level is nonzero and an optimum occurs at an intermediate gap spacing. The peak is created by the competition between increasing the sensitivity of the sensor but decreasing the magnitude of the signal, which is roughly proportional to the area enclosed by the secondary elements, as the gap spacing is increased. For FIGS. 22A and 22B, the simulated voltages ranged from 0.1 to approximately 4 mV. When the noise level is small compared to the measured signals, the optimal gap size approaches its maximum allowable value. As the noise level increases, the optimal gap spacing decreases so that the magnitude of the sensor voltage remains comparable to the noise level. This behavior is illustrated in FIG. 22C for both the magnitude and phase of the voltage. Since both the magnitude and the phase are used in the measurement of the material properties, the region between the curves of FIG. 22C defines the region of optimum gap spacing for the sensor. It appears that a gap spacing of approximately $\lambda/8$ (1.0 mm in this case) will provide nearly optimal sensitivity for small noise levels less than approximately 0.1 mV. Clearly, reducing the noise level by, for example, improving the instrumentation electronics allows sensors with enhanced sensitivity and deeper depths of penetration to be designed, fabricated and utilized.

Figure 12:
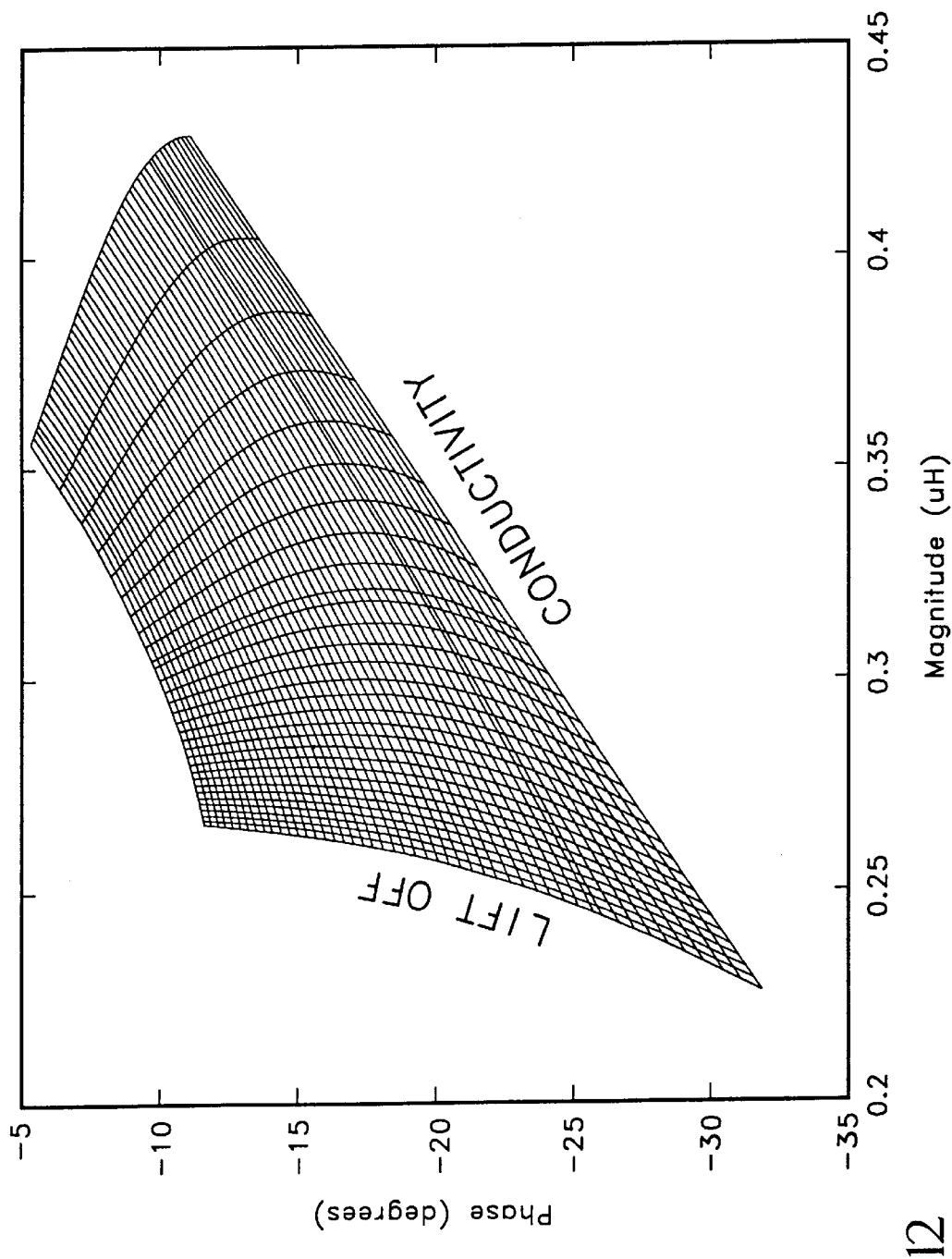
FIG. 12 is a graph measurement grid of lift off and conductivity for ferrous metal.

FIG. 12 shows a measurement grid phase versus magnitude of a piece of ferrous metal using a sensor as shown in FIG. 7 for varying combinations of the lift-off h and conductivity $\sigma$. In this specific embodiment shown, the primary wavelength, $\lambda$ is 8 mm, the primary width is 0.6 mm, the secondary width is 0.2 mmn, and the primary to secondary gap is 0.8 mm. Nominal valves for the lift-off h is 6.35 mils and for the conductivity is 460000 s/m.

Figure 13:
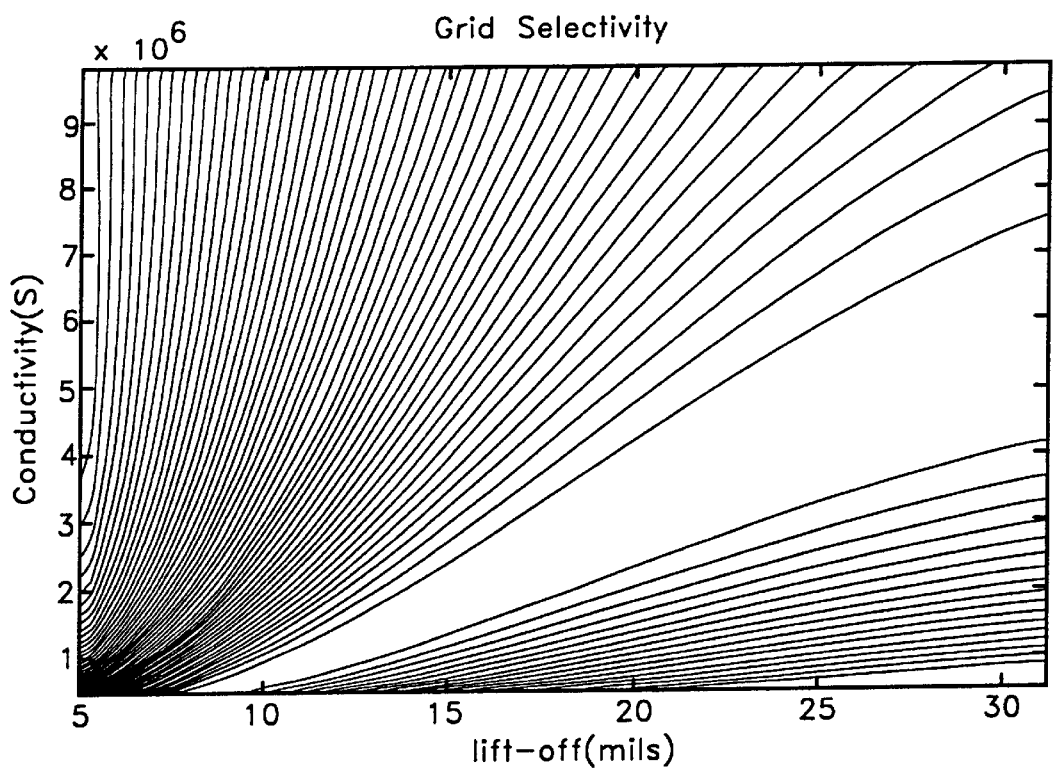
FIG. 13 is a grid selectivity graph of conductivity versus lift-off for the grid of FIG. 12.
Figure 14:
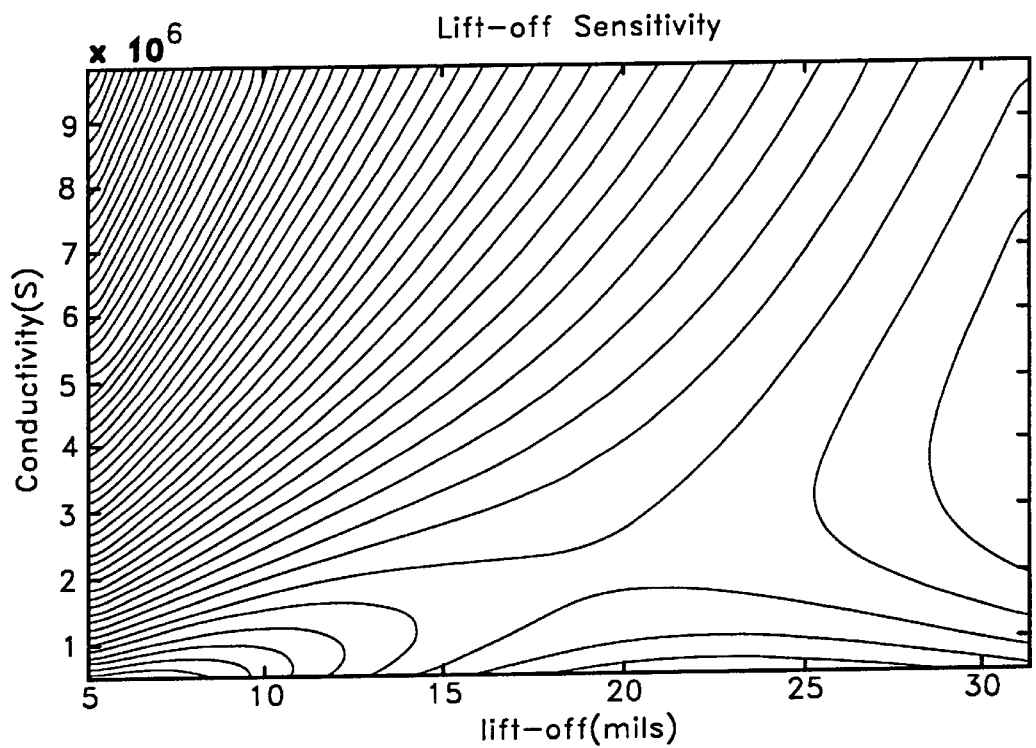
FIG. 14 is a lift-off sensitivity graph of conductivity versus lift-off for the grid of FIG. 12.
Figure 15:
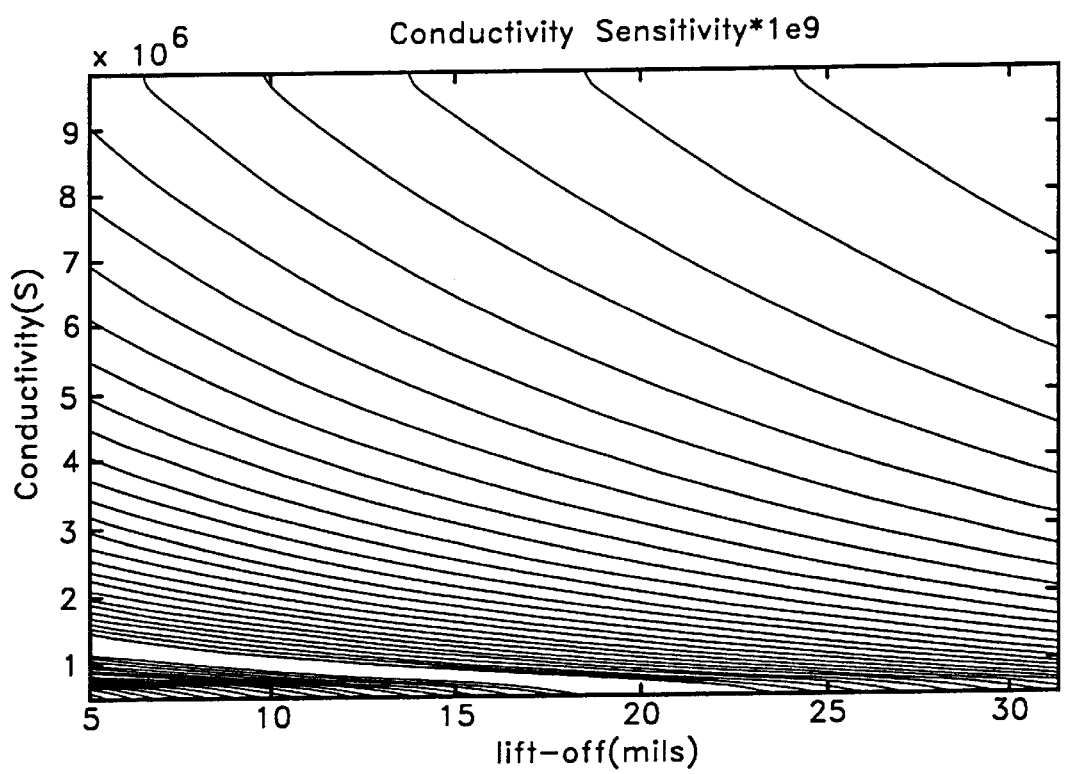
FIG. 15 is a conductivity sensitivity graph with parameters of conductivity versus lift-off for the grid of FIG. 12.
Figure 16:
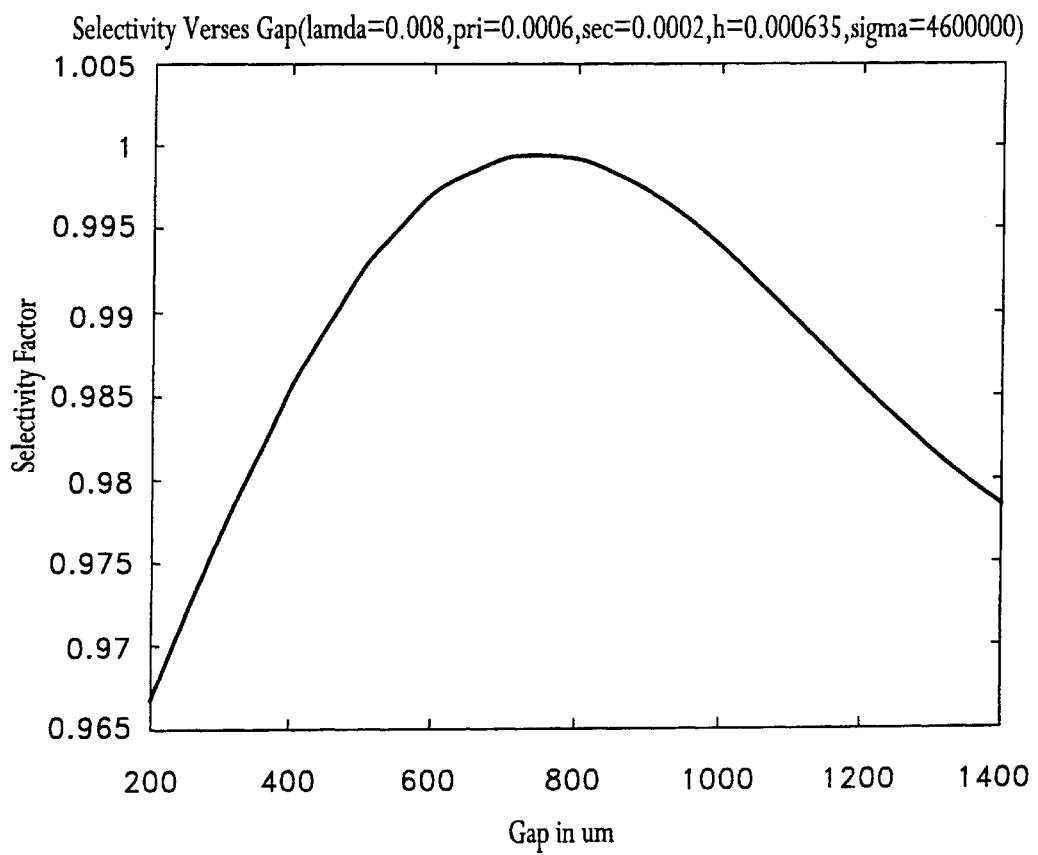
FIG. 16 is a graph of selectivity versus gap for the parameters listed on the graph.

FIG. 13 grid selectivity graph of conductivity versus lift-off; FIG. 14 is a lift-off sensitivity graph of conductivity versus liftoff; FIG. 15 is a conducting sensitivity graph with parameters conductivity versus liftoff. These three graphs show that increasing the gap does increase sensitivity at given depth and depth of sensitivity for a given sensor wavelength. This is further illustrated in FIG. 16 through 19.

Figure 20:
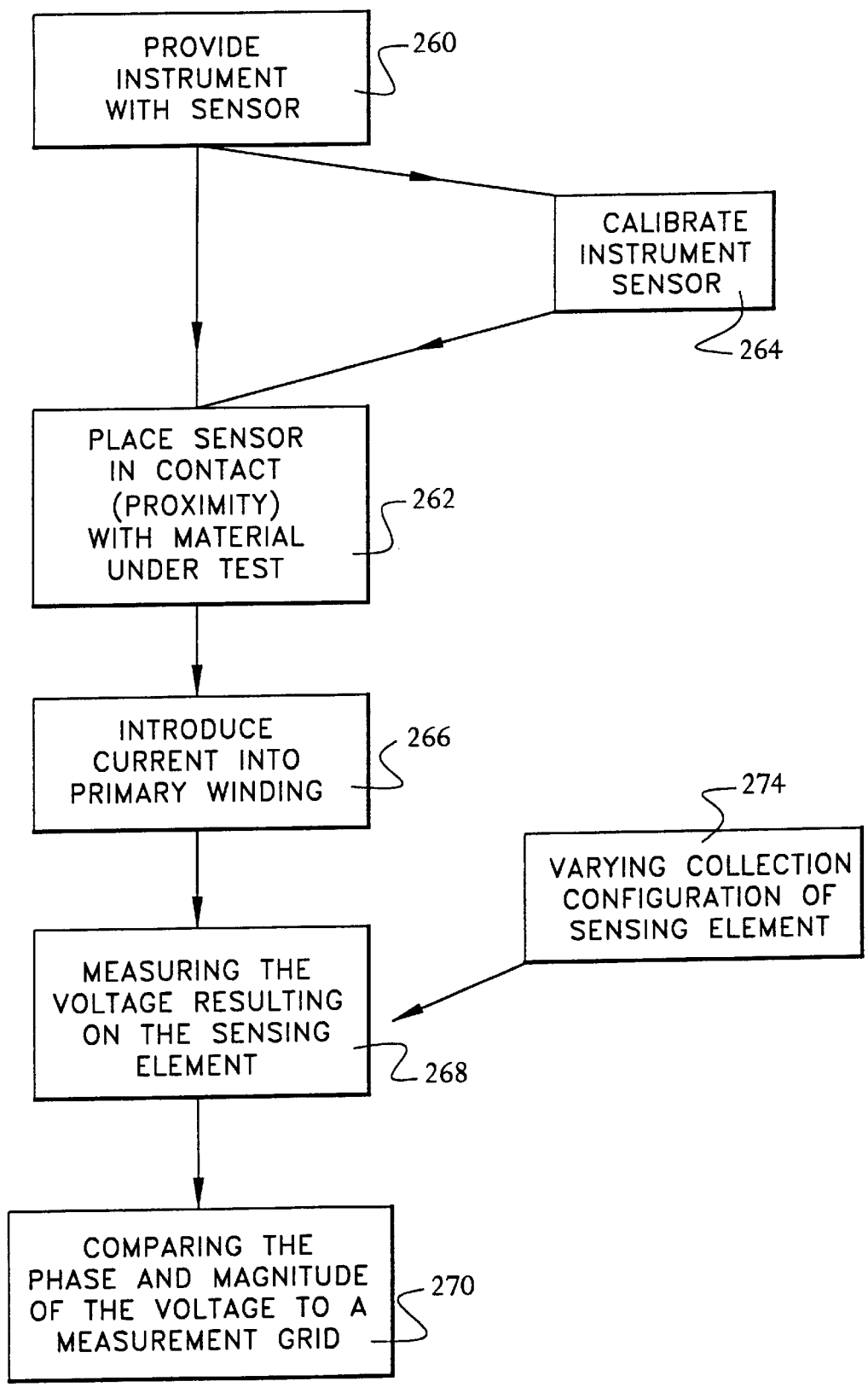
FIG. 20 is a flowchart of the process for measuring properties of the material under test.

FIG. 20 is a flowchart of the method of determining the properties of the material. The user prepares the instrument with sensor 260 such as the instrument described in FIGS. 1 and 10. The sensor is placed in contact or in proximity with the material under test 262. It is recognized and preferred to calibrate the instrument and sensor 264 prior to performing the determination of the materials property. A current is introduced into the primary winding 266 with resulting voltage on the sensing element measured 268. The phase and magnitude of this resulting voltage is compared to a measurement grid 270. The description of measurement grids and continuum models is described in U.S. patent application Ser. No. 07/803,504, entitled, "Magnetometer Having Periodic Winding Structure and Material Property Estimator" filed on Dec. 6, 1991 by Goldfine and Melcher which issued on Sep. 26, 1995 as U.S. Pat. No. 5,453,689, the entire contents of which are incorporated herein by reference.

These sensors have the sensing elements grouped in various combinations as discussed above with respect to FIGS. 3 through 9. In another embodiment, the property estimator through the RIM multiplexer or a multiplexer close to the sensor can select and group the sensing elements in various configuration where there are more than one group. Therefore all the sensing elements can be grouped together for absolute measurements for use with the grid method as discussed above or the resulting voltage measured on the sensing elements can be differentially applied by comparing the differences between neighboring or distant sensing elements to increase the sensitivity to a crack or local anomaly, while maintaining lift-off compensation at each sensing element. The sensing elements to be compared could be adjacent secondary elements in a single wavelength, distant secondary elements further away over a section, a material or air that can serve as a reference, and/or combinations of secondary elements. The varying of sensor arrays is represented as box 274 in FIG. 20.

While this invention has been particularly shown and described with references to preferred embodiments thereof, it will be understood by those skilled in the art that various changes in form and details may be made therein without departing from the spirit and scope of the invention as defined by the appended claims.

For example, the sensing elements in some of the sensors can be combined together to achieve an absolute measurement for use with the Grid Method or measured differentially to increase sensitivity. It is recognized that the absolute and the differential use of a sensing elements in a single array can also be used for Dielectric arrays.

The MWM sensors can be fabricated in several embodiments. These can have either multiple periods, a single period (i.e., only one period of a sine wave is produced by the field shaping primary), or a fraction of a period (e.g. half). While the embodiments will be described with respect to preferred embodiments for a particular size range, such descriptions are not meant to limit particular sizes to particular embodiments.

One embodiment of the sensor 30 is fabricated by deposition and selective removal of a conducting material on a thin film nonconducting substrate as seen in FIGS. 3–8. This printed conducting material is considered a wire. This method of sensor construction allows the sensor to be very thin and of very low mass. It can be configured as an array for surface scanning by movement of an array to build images (with preferred sensing elements as small as 1 mm by 3 mm and sensor footprints ranging from 3 mm by 6 mm to over 1 m by 1 m). In this embodiment the primary and sensing elements are confined to a single plane. Differencing of elements for differential mode is performed by a separate circuit along with the multiplexing function.

In certain embodiments in which a large surface is to be scanned at one time, the array can be several square feet or several hundred square feet. In certain embodiments having arrays of over a square foot, arrays of secondary winding elements provide spatial resolution of indications on the order of an inch. This effectively maps the conductivity of the structure in fine increments to detect abnormalities as described below.

Figure 21:
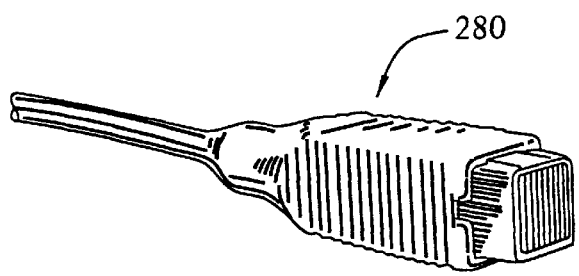
FIG. 21 illustrates an improved MWM probe design with a removable foam sensor tip.

As improved probe holders 280, such as shown in FIG. 21, can also be used with the half inch by half inch footprint MWM shown. Smaller probes are also possible. The foam tip conforms to curved parts and can be removed easily and replaced if damaged.

The measurement grid methods for calibration and property estimation offer the unique capability to measure absolute electrical conductivity without the use of calibration standards. Calibration is accomplished by holding the MWM probe in air, away from any conducting objects. The MWM sensor is capable of measuring within less than 1% IACS (international copper standard=5.8E7 S/m) absolute accuracy for conductivity ranging from 0.5% to 100% IACS. The MWM sensor is cable of measuring on magnetizable material such as steel without requiring recalibration. For example, a painting coating thickness can be measured on steel, without thickness standards, to within one micron.

Relative conducting differences of less than 0.01% IACS can be resolved.

The MWM sensor is driven by an AC current and its response is measured by an impedance analyzer. In a preferred embodiment, a circuit board-level, multi-frequency impedance instrument having a range of 10 kHz–2.5 MHZ is used. The response is compared to the continuum models, described below. The sensor response which is in the terms of impedance phase and magnitude is converted into material properties or conditions of interest, such as conductivity and proximity or conductivity and lift-off.

In addition to permitting precise determinations of material properties, the MWM modeling software also incorporates methods to identify operating conditions that provide maximum sensitivity and selectivity (the ability to measure two or more properties independently), without running extensive experiments. The identification of operating condition is described in further detail in U.S. Pat. No. 5,015,951 titled "Apparatus and Methods for Measuring Permeability and Conductivity in Materials Using Multiple Wavenumber Magnetic Interrogations" which issued on May 14, 1991 and a U.S. patent application Ser. No. 08/702,276 titled "Meandering Winding Test Circuit" and filed on Aug. 23, 1996, the entire contents of which are incorporated herein by reference.

Grid measurement algorithms permit the integration of impedance measurement data at multiple frequencies, multiple winding spatial wavelengths, and multiple lift-offs (by moving the MWM sensor, using a roving sensing element, or roving arrays). This integration is used in conjunction with the array calibration discussed below. Measurement grids provide a generalized and robust approach to a wide variety of applications, and permit rapid adaptation to new applications with varied material constructs and properties of interest. The result is a multi-dimensional identification algorithm that provides robust, reproducible, and high confidence microcrack detection capability. It provides real-time (fast) measurements, enabled by table look-up from stored measurement grids.

Note that roving arrays might be used with a deep penetrating primary as described in U.S. patent application Ser. No. 09/003,390, entitled, "Magnetometer and Dielectrometer Detection of Subsurface Objects" which was filed on Jan. 6, 1998, the entire contents of which is incorporated by reference. The array might be used for object imaging and tracking with the object beyond the roving element array or between the roving element array and the primary (e.g., as tracking a metal object in a human patient).

Measurement grids are tables produced by the continuum models of the MWM and in a preferred embodiment are graphically displayed. The measurement grids are used to convert the MWM impedance magnitude and phase measurements into material properties or material proximity. The real-time table look-up process is described in U.S. patent application Ser. No. 08/702,276 which is titled "Meandering Winding Test Circuit" which was filed on Aug. 23, 1996, the entire contents of which is incorporated by reference.

The grid measurement approach allows for detection and discrimination of clusters of cracks including microcracks. The measurement grids also provide a unique tool for rapid field calibration of sensing arrays.

To generate measurement grids, the material conductivity (or other property of interest) is first estimated using calibration standards or values from the literature. (This estimate merely serves to define the general region of interest in which to run the models to generate predicted sensor response.) The continuum models of the MWM then predict sensor response, in terms of phase and magnitude, using the selected ranges of conductivity and lift-off. This type of grid is composed of lines of constant lift-off intersecting lines of constant conductivity. These grids are generated off-line and then provide a real-time (fractions of a second) measurement capability in the field.

The combination of MWM design and operational features with the grid measurement approach provides a repeatable procedure to detect properties of the material under test.

What is claimed is:

1. A sensor comprising:
    a primary winding meandering in a back and forth square wave-like pattern and having a plurality of parallel legs, a half wavelength defined by the space between a pair of adjacent parallel legs;
    a plurality of sensing elements, the sensing elements interposed between the legs of the primary winding;
    dummy sensing elements located in half wavelengths at ends of the primary winding for maintaining the periodicity of the field for the sensing elements.

2. The sensor of claim 1 wherein sensing elements opening to one side of the primary winding are connected in series to one another and sensing elements opening to the other side of the primary winding are connected to one another.

3. The sensor of claim 2 further comprising at least one additional sensing element near the end of the primary winding and defining a small pixel for detection of the edge of a material under test.

4. The sensor of claim 1 wherein each of the sensing elements has a pair of distinct leads.

5. The sensor of claim 1 wherein the primary winding has a plurality of connecting portions for connecting the plurality of parallel legs and wherein each of the sensing elements has an end which is spaced from a connection portion of primary winding within a range of one-quarter and one-half of wavelength.

6. The sensor of claim 1 further comprising leads to the sensing elements, the leads shouldered in from the sensing elements to minimize coupling of the leads of the sensing elements to the primary winding.

7. A sensor comprising:
    a primary winding meandering in a back and forth square wave-like pattern and having a plurality of parallel legs, a half wavelength defined by the space between a pair of adjacent parallel legs; and
    a plurality of sensing elements, the sensing elements interposed between the legs of the primary winding, the sensing elements opening to one side of the primary winding being connected in a plurality of distinct groups and the sensing elements opening to the other side of the primary winding being connected in a plurality of distinct groups.

8. The sensor of claim 7 wherein at least one group of the one side overlaps a plurality of groups on the other side.

9. The sensor of claim 8 wherein the gap between the sensing element and the parallel legs of the primary winding is approximately an eighth of a wavelength for minimizing coupling of shorter wavelength modes.

10. The sensor of claim 8 wherein the primary winding has a plurality of connecting portions for connecting the plurality of parallel legs and wherein each of the sensing elements has an end which is spaced from a connection portion of primary winding within a range of one-quarter and one-half of wavelength.

11. The sensor of claim 8 further comprising leads to the sensing elements, the leads shouldered in from the sensing elements to minimize coupling of the leads of the sensing elements to the primary winding.

12. The sensor of claim 7 wherein at least one group on the one side has less sensing elements than the at least one group on the other side and all the sensing elements of the one group on the one side are interposed between sensing elements of the one group of the other side.

13. The sensor of claim 12 wherein the gap between the sensing element and the parallel legs of the primary winding is approximately an eighth of a wavelength for minimizing coupling of shorter wavelength modes.

14. The sensor of claim 12 wherein the primary winding has a plurality of connecting portions for connecting the plurality of parallel legs and wherein each of the sensing elements has an end which is spaced from a connection portion of primary winding within a range of one-quarter and one-half of wavelength.

15. The sensor of claim 12 further comprising leads to the sensing elements, the leads shouldered in from the sensing elements to minimize coupling of the leads of the sensing elements to the primary winding.

16. A sensor comprising:
   a primary winding meandering in a back and forth square wave-like pattern and having a plurality of parallel legs, a half wave length defined by the space between a pair of adjacent parallel legs;
   a plurality of sensing elements, the sensing elements interposed between the legs of the primary winding; and
   a gap between the sensing element and the parallel legs of the primary winding is approximately an eighth of a wavelength for minimizing coupling of shorter wavelength modes.

17. The sensor of claim 16 further comprising a pair of dummy sensing elements, each dummy sensing element located at an end of the primary winding in the last half wavelength of primary winding for maintaining the periodicity of the field for the sensing element.

18. The sensor of claim 16 wherein the primary winding has a plurality of connecting portions for connecting the plurality of parallel legs and wherein each of the sensing elements has an end which is spaced from a connection portion of primary winding within a range of one-quarter and one-half of wavelength.

19. The sensor of claim 16 further comprising leads to the sensing elements, the leads shouldered in from the sensing element to minimize coupling of the leads of the sensing elements to the primary winding.

20. An instrument for measuring property of a material comprising
   a sensor having
      a primary winding meandering in a square wave pattern and having a plurality of parallel legs, a half wave length defined by the space between a pair of adjacent parallel legs; and
      a plurality of sensing elements, the sensing elements interposed between the legs of the primary winding;
   a probe head for holding the sensor;
   an impedance analyzer for inputting an input current or voltage source at a temporal excitation frequency and measuring the output from the sensing elements, the analyzer having remote analog components; and
   a property analyzer for analysis of the measured output.

21. The instrument of claim 20 wherein the probe head contains a differential amplifier therein minimizing unmodeled change in the sensor behavior.

22. The sensor of claim 21 further comprising a pair of dummy sensing elements, each dummy sensing element located at an end of the primary winding in the last half wavelength of primary winding for maintaining the periodicity of the field for the sensing element.

23. The sensor of claim 21 wherein the primary winding has a plurality of connecting portions for connecting the plurality of parallel legs and wherein each of the sensing elements has an end which is spaced from a connection portion of primary winding between a range of one-quarter and one-half of wavelength.

24. The instrument of claim 21 further comprising a grid model in the property analyzer.

25. The instrument of claim 20 further comprising a remote instrument module spaced from the property analyzer and containing an analog portion of the impedance analyzer for increasing the signal to noise ratio.

26. The sensor of claim 25 further comprising a pair of dummy sensing elements, each dummy sensing element located at an end of the primary winding in the last half wavelength of primary winding for maintaining the periodicity of the field for the sensing element.

27. The sensor of claim 25 wherein the primary winding has a plurality of connecting portions for connecting the plurality of parallel legs and wherein each of the sensing elements has an end which is spaced from the connection portion of primary winding between a range of one-quarter and one-half of wavelength.

28. The instrument of claim 25 further comprising a grid model in the property analyzer.

29. The instrument of claim 20 further comprising a remote instrument module spaced from the property analyzer and containing the independently controllable amplifiers for the input current and measurement voltage for optimizing or tuning the electronics to a representative range in properties for the material under test.

30. The sensor of claim 29 further comprising a pair of dummy sensing elements, each dummy sensing element located at an end of the primary winding in the last half wavelength of primary winding for maintaining the periodicity of the field for the sensing element.

31. The sensor of claim 29 wherein the primary winding has a plurality of connecting portions for connecting the plurality of parallel legs and wherein each of the sensing elements has an end which is spaced from the connection portion of primary winding between a range of one-quarter and one-half of wavelength.

32. The instrument of claim 29 further comprising a grid model in the property analyzer.

33. A method of calibration of a sensor comprising the following steps:
   providing a sensor having a primary winding meandering in a square wave pattern with a plurality of parallel legs and a plurality of sensing elements with the sensing elements interposed between the legs of the primary winding;
   connecting the sensor to an impedance analyzer;
   placing the sensor in the air away from a material under test;
   introducing a current into the primary winding;
   measuring the voltage resulting on the sensing elements using the impedance analyzer; and
   aligning the phase and magnitude of the impedance to a measurement grid.

34. The method of claim 33 wherein the step of aligning comprises shifting and scaling the measured impedance.

35. The method of claim 33 wherein the step of aligning comprises shifting the measurement grid.

36. The method of claim 33 further comprising varying a known property to verify and tune calibration.

37. The method of claim 36 wherein the property is lift-off.

38. The method of claim 36 wherein the property is conductivity.

39. The method of claim 36 wherein the property is permeability.

40. A method of measuring a property of a material comprising the following steps:

provinding a sensor having a primary winding meandering in a square wave pattern with a plurality of parallel legs and a plurality of sensing elements with the sensing elements interposed between the legs of the primary winding;

connecting the sensor to an impedance analyzer;

placing the sensor in the air away from a material under test;

introducing a current into the primary winding;

measuring the voltage resulting on the sensing elements using the impedance analyzer;

aligning the phase and magnitude of the impedance to a measurement grid;

moving the sensor in proximity to the material under test;

introducing a current into the primary winding;

measuring the voltage resulting on the sensing elements using the impedance analyzer; and converting the phase and magnitude of the impedance using the measurement grid to determine at least one unknown property of interest.

41. A method of measuring a property of a material comprising the following steps:

providing a sensor having a primary winding meandering in a square wave pattern with a plurality of parallel legs and a plurality of sensing elements with the sensing elements interposed between the legs of the primary winding, wherein the sensor elements opening to one side of the primary winding are connected in a plurality of distinct groups and sensing elements opening to the other side of the primary winding are connected in a plurality of distinct groups and each of the groups of the one side having at least one sensing element located interposed between sensing elements of a group on the other side and at least one sensing element located interposed between sensing elements of a second group on the other side, therein the groups overlapping;

connecting the sensor to an impedance analyzer;

moving the sensor in proximity to a material under test;

introducing a current into the primary winding;

measuring the voltage resulting on the sensing elements using the impedance analyzer; and converting the phase and magnitude of the impedance using the measurement grid to determine at least one unknown property of interest.

42. A method of measuring a property of a material comprising the following steps:

providing a sensor having a primary winding meandering in a square wave pattern with a plurality of parallel legs and a plurality of sensing elements with the sensing elements interposed between the legs of the primary winding, wherein the sensor elements opening to one side of the primary winding are connected in a plurality of distinct groups and sensing elements opening to the other side of the primary winding are connected in a plurality of distinct groups and at least one group on the one side has less sensing elements that the at least one group on the other side and all the sensing elements of the one group on the one side are interposed between sensing elements of the one group of the other side;

connecting the sensor to an impedance analyzer;

moving the sensor in proximity to a material under test;

introducing a current into the primary winding;

measuring the voltage resulting on the sensing elements using the impedance analyzer; and converting the phase and magnitude of the impedance using the measurement grid to determine at least one unknown property of interest.

43. A method of measuring a property of a material comprising the following steps:

providing a sensor having a primary winding meandering in a square wave pattern with a plurality of parallel legs and a plurality of sensing elements with the sensing elements interposed between the legs of the primary winding;

connecting the sensor to an impedance analyzer;

moving the sensor in proximity to a material under test;

introducing a current into the primary winding;

measuring the voltage resulting on the sensing elements using the impedance analyzer; and converting the phase and magnitude of the impedance using a measurement grid wherein all the sensing elements are grouped together for absolute measurements.

44. A method of measuring a property of a material comprising the following steps:

providing a sensor having a primary winding meandering in a square wave pattern with a plurality of parallel legs and a plurality of sensing elements with the sensing elements interposed between the legs of the primary winding;

connecting the sensor to an impedance analyzer;

moving the sensor in proximity to a material under test;

introducing a current into the primary winding;

measuring the voltage resulting on the sensing elements using the impedance analyzer; and converting the phase and magnitude of the impedance using a measurement grid of at least one sensing element to determine the absolute measurement of at least one property and measuring the differences between sensing elements to increase the sensitivity to at least one unknown property.

* * * * *